United States Patent [19]

Ohta et al.

[11] Patent Number: 5,344,927
[45] Date of Patent: Sep. 6, 1994

[54] TETRAHYDROBENZIMIDAZOLE DERIVATIVES AND PHARMACEUTICAL COMPOSITIONS CONTAINING SAME

[75] Inventors: Mitsuaki Ohta; Tokuo Koide; Takeshi Suzuki; Akira Matsuhisa, all of Ibaraki; Keiji Miyata, Tokyo; Junya Ohmori, Ibaraki; Isao Yanagisawa, Tokyo, all of Japan

[73] Assignee: Yamanouchi Pharmaceutical Co., Ltd., Tokyo, Japan

[21] Appl. No.: 39,633

[22] Filed: Mar. 30, 1993

Related U.S. Application Data

[63] Continuation of Ser. No. 713,890, Jun. 12, 1991, abandoned, which is a continuation of Ser. No. 567,949, Aug. 15, 1990, abandoned, which is a continuation-in-part of Ser. No. 470,950, Jan. 26, 1990, abandoned.

[30] Foreign Application Priority Data

| Feb. 2, 1989 | [JP] | Japan | 1-25397 |
| Feb. 28, 1989 | [JP] | Japan | 1-48897 |
| Oct. 20, 1989 | [JP] | Japan | 1-273444 |
| Dec. 28, 1989 | [JP] | Japan | 1-342939 |

[51] Int. Cl.$^5$ ............... A61K 31/505; A61K 31/47; C07D 235/04; C07D 239/42; C07D 401/00
[52] U.S. Cl. .................... 544/31; 544/105; 544/331; 546/121; 546/159; 546/168; 548/139; 548/184; 548/185; 548/304.7; 548/305.1; 548/305.4; 548/305.7; 548/306.1
[58] Field of Search ............ 548/305.1, 305.4, 304.7, 548/139, 305.7, 306.1, 184, 185; 544/31, 105, 331; 546/121, 159, 168, 371; 514/229.8, 230.5, 256, 299, 314, 339, 363, 367, 394, 225.8

[56] References Cited

U.S. PATENT DOCUMENTS

| 3,772,315 | 11/1973 | Regel et al. | 548/306.1 X |
| 3,873,558 | 3/1975 | Grenda et al. | 548/306.1 X |
| 3,907,700 | 9/1983 | Grier | 252/300 |
| 4,414,214 | 11/1989 | Habichi et al. | 424/248.51 |
| 4,820,757 | 4/1989 | Spang et al. | 524/93 |
| 5,008,397 | 4/1991 | Spang et al. | 548/331 |
| 5,149,700 | 9/1992 | Ellingboe et al. | 514/275 |

*Primary Examiner*—Floyd D. Higel
*Attorney, Agent, or Firm*—Burgess, Ryan and Wayne

[57] ABSTRACT

A tetrahydrobenzimidazole derivative represented by formula (I):

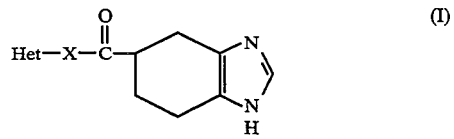

wherein Het represents a heterocyclic group which may be substituted with 1 to 3 substituents selected from the group consisting of a lower alkyl group, a lower alkenyl group, a lower alkynyl group, a cycloalkyl-lower alkyl group, an aralkyl group, a lower alkoxy group, a nitro group, a hydroxyl group, a lower alkoxy-carbonyl group, and a halogen atom; and X represents a single bond or —NH— which is bonded to the carbon atom or nitrogen atom of the heterocyclic ring, or a pharmaceutically acceptable salt thereof.

The compound of formula (I) and a salt thereof exhibits antagonism against 5-HT$_3$ receptor.

32 Claims, No Drawings

TETRAHYDROBENZIMIDAZOLE DERIVATIVES AND PHARMACEUTICAL COMPOSITIONS CONTAINING SAME

This application is a continuation of application Ser. No. 07/713,890, filed Jun. 12, 1991, now abandoned, which is a continuation of application Ser. No. 07/567,949, filed Aug. 15, 1990, now abandoned, which in turn is a continuation-in-part of application Ser. No. 07/470,950, filed Jan. 26, 1990, now abandoned.

BACKGROUND OF THE INVENTION

1. Field of the Invention

This invention relates to a tetrahydrobenzimidazole derivative represented by formula (I) shown below or a pharmaceutically acceptable salt thereof which are useful as a 5-HT$_3$-receptor antagonist

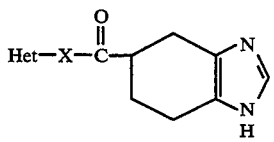

wherein Het represents a heterocyclic group which may be substituted with 1 to 3 substituents selected from the group consisting of a lower alkyl group, a lower alkenyl group, a lower alkynyl group, a cycloalkyl-lower alkyl group, an aralkyl group, a lower alkoxy group, a nitro group, a hydroxyl group, a lower alkoxycarbonyl group, and a halogen atom; and X represents a single bond or —NH— which is bonded to the carbon atom or nitrogen atom of the heterocyclic group.

2. Description of the Related Art

Conventionally known antagonists to 5-HT$_3$-receptors include azabicyclo compounds as disclosed in British Patents 2,125,398, 2,166,726, 2,166,727, and 2,126,728 (corresponding to JP-A-59-36675 and JP-A-59-67284, the term "JP-A" as used herein means an "unexamined published Japanese patent application"), tetrahydrocarbazole compounds as disclosed in British Patent 2,153,821 (corresponding to JP-A-60-214784), and azabicyclo compounds as disclosed in EP 280,444 (corresponding to JP-A-61-275276).

SUMMARY OF THE INVENTION

The inventors have conducted extensive research on compounds showing antagonism against 5-HT$_3$-receptors. As a result, they have found that the compound represented by formula (I) is a novel compound exhibiting high 5-HT$_3$-receptor antagonistic activity and thus reached the present invention. The compounds according to the present invention are entirely different in structure from any of the above-described known 5-HT$_3$-receptor antagonists.

DETAILED DESCRIPTION OF THE INVENTION

In formula (I), the heterocyclic group as represented by Het includes residues of monocyclic or condensed heterocyclic rings. Specific examples of the heterocyclic ring are pyrrolidine, piperidine, piperazine, morpholine, pyrrole, furan, thiophene, imidazole, oxazole, ithiazole, pyrazole, isoxazole, isothiazole, triazole, thiadiazole, oxadiazole, pyridine, pyridazine, pyrimidine, pyrazine, 4H-cyclopentathiazole, indole, isoindole, 2,3-dihydroindole (indoline), isoindoline, hydroxyindole, indazole, indolizine, benzothiophene, benzofuran, benzothiazole, benzimidazole, benzoxazole, 4,5,6,7-tetrahydrobenzothiophene, 2,3-dihydrobenzimidazol-2-one, quinoline, isoquinoline, 1,2,3,4-tetrahydroquinoline, 1,2,3,4-tetrahydroisoquinoline, 1,4-benzoxazine, phenothiazine, carbazole, β-carboline, etc.

The heterocyclic group may have a substituent(s) at optional position(s), such as a lower alkyl group, a lower alkenyl group, a lower alkynyl group, a cycloalkyl-lower alkyl group, an aralkyl group, a lower alkoxy group, a nitro group, a hydroxyl group, a lower alkoxycarbonyl group, a halogen atom, etc.

Unless otherwise specified, the term "lower alkyl group" as used herein means a straight chain or branched alkyl group having from 1 to 6 carbon atoms. Specific examples of the lower alkyl group are methyl, ethyl, propyl, butyl, pentyl, hexyl, isopropyl, isobutyl, t-butyl, isopentyl, t-pentyl, isohexyl groups, etc.

Examples of the "lower alkenyl group" include vinyl, allyl, 1-propenyl, 2-butenyl, isopropenyl groups, etc. Examples of the "lower alkynyl group" include ethnyl, 2-propynyl groups, etc. Examples of the "cycloalkyl-lower alkyl group" include cyclopropylmethyl, cyclopentylmethyl, cyclohexylmethyl, cyclohexylethyl, cycloheptylmethyl groups, etc. Examples of the "aralkyl group" include benzyl, phenethyl groups, etc. Examples of the "lower alkoxy group" include methoxy, ethoxy, propoxy, butoxy, pentyloxy, hexyloxy, isopropoxy, isobutoxy, t-butoxy, isopentyloxy, t-pentyloxy, isohexyloxy, 2-ethylbutoxy groups, etc. Examples of the "lower alkoxycarbonyl group" include methoxycarbonyl, ethoxycarbonyl, propoxycarbonyl, isopropoxycarbonyl, butoxycarbonyl, t-butoxycarbonyl, pentyloxycarbonyl, hexyloxycarbonyl groups, etc.

The halogen atom includes chlorine, bromine, iodine, and fluorine atoms.

Of the compounds represented by formula (I), preferred are those wherein Het is represented by formula:

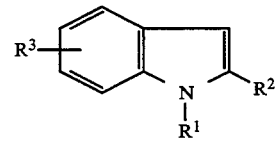

wherein $R^1$ represents a hydrogen atom, a lower alkyl group, a lower alkenyl group, a lower alkynyl group, a cycloalkyl-lower alkyl group, or an aralkyl group; $R^2$ represents a hydrogen atom, a lower alkyl group, or an aralkyl group; and $R^3$ represents a hydrogen atom, a lower alkoxy group, a nitro group, a hydroxyl group, a lower alkoxycarbonyl group, or a halogen atom; and X represents a single bond, and those wherein Het represents a nitrogen-containing heterocyclic group; and X is a single bond connected to the nitrogen atom of the nitrogen-containing heterocyclic ring.

Also included under the present invention are salts of some of the compounds of formula (I). Examples of such salts include salts with inorganic bases, e.g., sodium and potassium; salts with organic bases, e.g., ethylamine, propylamine, diethylamine, triethylamine, morpholine, piperidine, N-ethylpiperidine, diethanolamine, and cyclohexylamine; salts with basic amino acids, e.g., lysine and ornithine; ammonium salts; salts with mineral acids, e.g., hydrochloric acid, sulfuric acid, phosphoric acid, and hydrobromic acid; salts with organic acids, e.g., acetic acid, oxalic acid, succinic acid, citric acid, maleic acid, malic acid, fumaric acid, dibenzoyl tartaric acid, tartaric acid, and methanesulfonic acid; and salts with acidic amino acids, e.g., glutamic acid and aspartic acid.

While the compounds according to the present invention are represented by formula (I), the present invention further includes tautomers of these compounds, i.e., compounds represented by formula:

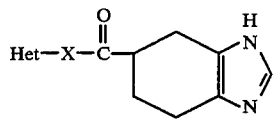

Furthermore, the compounds of the present invention carry asymmetric carbon atoms in the molecule, and all the isomers assigned to these asymmetric carbon atoms, such as optically active compounds, racemates, diastereomers, etc., are included in the compounds according to the present invention.

Processes for preparing the compounds according to the present invention are described below.

PROCESS 1 (Amidation):

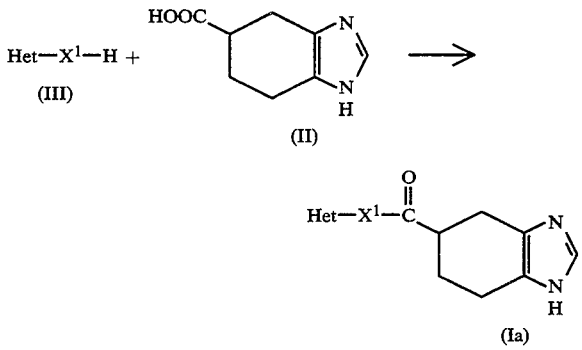

wherein Het is as defined above; and $X^1$ represents a single bond connected to the nitrogen atom of the heterocyclic group, or $X^1$ represents —NH— connected to the carbon atom of the heterocyclic group.

The compound (Ia) of the present invention can be obtained by reacting an amine, an amide, or urea represented by formula(III) with 4,5,6,7-tetrahydrobenzimidazole-5-carboxylic acid represented by formula (II) or a reactive derivative thereof.

The reaction is carried out by any of various known processes for amide linkage formation. Solvents to be used are not particularly limited and include dioxane, diethyl ether, tetrahydrofuran, chloroform, ethyl acetate, and dimethylformamide.

The compound (II) is subjected to the reaction with the compound (III) as being either in the form of a free acid or in the form of a reactive derivative thereof, e.g., an acid halide, an acid anhydride, an acid azide, and various active esters generally used in peptide syntheses. In the former case, the amide linkage formation can be effected by using any of commonly employed condensing agents, for example, N,N-dicyclohexylcarbodiimide.

In some cases depending on the kind of the reactive derivative of the compound (II), the reaction is preferably carried out in the presence of a base, such as inorganic bases, e.g., sodium hydrogencarbonate, potassium hydrogencarbonate, sodium carbonate, and potassium carbonate; and organic bases, e.g., triethylamine, diisopropylethylamine, dimethylaniline, and pyridine.

The compound (III) is usually used as it is or, if desired, after being converted to an alkali metal salt thereof.

The compound (III) is desirably used in an equimolar or excessive amount with respect to the compound (II) or a reactive derivative thereof.

The reaction is possibly carried out at room temperature, under cooling, or under heating as selected depending on the kind of the amide linkage reaction mode but usually at room temperature or under cooling.

PROCESS 2:

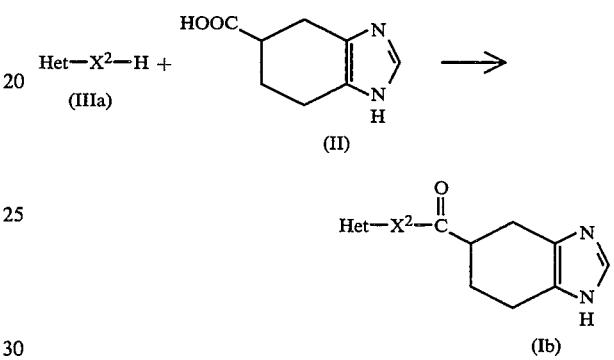

wherein Het is as defined above; and $X^2$ represents a single bond connected to the carbon atom of the heterocyclic ring as represented by Het.

The compound (Ib) can be obtained by reacting a heterocyclic compound represented by formula (IIIa) with a carboxylic acid represented by formula (II) or a reactive derivative thereof.

The reaction can be carried out by any of various known processes for synthesizing carbonyl compounds using a carboxylic acid or a derivative thereof.

Where a carboxylic acid of formula (II) is employed; the reaction with the compound of formula (IIIa) is a dehydrating condensation reaction using polyphosphoric acid, for instance, as a condensing agent. The reaction is carried out with or without a solvent. Solvents which can be used are not limited as long as inert to the reaction, but, usually, solvents having an appropriate boiling point are selected taking the reaction temperature into consideration. Examples of suitable solvents are decalin, tetralin, diglyme, etc. The reaction is effected at room temperature or preferably under heating.

Where an acid halide of the carboxylic acid of formula (II) is employed, the reaction is a Friedel-Crafts reaction which can be carried out by known processes or various modifications thereof using a Lewis acid, e.g., aluminum chloride, ferric chloride, stannic chloride, boron trifluoride ethyl etherate, and titanium tetrachloride. Solvents inert to the reaction may be employed preferably being selected depending on the kind of the Lewis acid used. Examples of usable solvents are acetonitrile and carbon disulfide. The reaction is performed at room temperature or, usually, under heating.

Where an acid amide of the carboxylic acid of formula (II) is employed, the reaction is a Vilsmeyer reaction, which is a known reaction mode frequently employed for synthesis of heterocyclic carbonyl compounds. Reagents for converting the acid amide to a Vilsmeyer complex include general halogenating agents, e.g., phosphorus pentachloride and phosphorus oxychloride. This reaction may be effected with or without a solvent. In using a solvent, various kinds of solvents can be employed as long as inert to the reaction. A suitable example of solvents is 1,2-dichloroethane. The reaction is performed at room temperature or under heating, and preferably under heating.

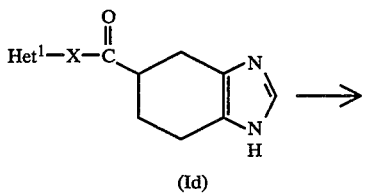

(Id)

(Ic)

wherein X is as defined above; $Het^1$ represents a heterocyclic group having —NH— in the ring thereof; and $Het^2$ represents a heterocyclic group in which the —NH— moiety in $Het^1$ is converted to

wherein $R^4$ represents a lower alkyl group, a lower alkenyl group, a lower alkynyl group, a cycloalkyl-lower alkyl group, or an aralkyl group.

This reaction is an N-alkylation reaction. The terminology "alkylation" as used herein means introduction of a lower alkyl, lower alkenyl, lower alkynyl, cycloalkyl-lower alkyl or aralkyl group. Any of various known alkylation techniques is applicable. For example, in case where the alkylation is carried out by direct N-alkylation using an alkylating agent, the reaction is conducted under cooling, at room temperature, or under heating, and preferably under cooling or at room temperature. Any solvent inert to the reaction, e.g., dioxane and dimethylformamide, may be employed. The reaction is effected in the presence of a base or by using an alkali metal salt of the compound (Id) at the amino group thereof. Examples of suitable alkylating agents include alkyl halides and alkyl sulfates. Examples of suitable bases include inorganic bases, e.g., sodium hydride, sodium hydrogencarbonate, potassium hydrogencarbonate, sodium carbonate, and potassium carbonate; and organic bases, e.g., triethylamine, diisopropylamine, dimethylaniline, and pyridine.

The thus prepared compound of the present invention is isolated and purified either in the free form or in the form of a salt through usual chemical means, such as extraction, crystallization, recrystallization, and various chromatographic techniques.

The compound as obtained in the form of a racemate can be led to stereochemically pure isomers by using an appropriate starting compound or by general resolution techniques (for example, a method comprising once obtaining a diastereomer salt with an ordinary optically active acid, e.g., dibenzoyl tartaric acid, followed by optical resolution).

The compounds according to the present invention and the salts thereof specifically inhibit transient bradycardia induced by serotonin in anesthetized rats as demonstrated by Test Example 1 hereinafter described and are thus believed to have antagonism against 5-$HT_3$-receptor. Therefore, the compounds of the present invention and the salts thereof are considered to suppress vomiting induced by anticancer agents, e.g., Cisplatin, or radiation and to be useful in the prevention and treatment of migraine, cluster headache, trigeminal neuralgia, anxiety, gastrointestinal disorders, peptic ulcer, irritable bowel syndrome, etc.

A pharmaceutical composition containing at least one of the compounds of the present invention or salts thereof as an active ingredient is prepared in various dose forms, such as tablets, powders, granules, capsules, pills, liquids, injections, suppositories, ointments, pastes, and the like using carriers, excipients and other additives conventionally used in pharmaceuticals. The preparation may be administered orally, inclusive of sublingual administration, or parenterally.

Carriers or excipients for pharmaceutical compositions include solid or liquid non-toxic pharmaceutically acceptable materials, e.g., lactose, magnesium stearate, starch, talc, gelatin, agar, pectin, gum arabic, olive oil, sesame oil, cocoa butter, ethylene glycol, and the like.

A clinical dose of the compound of the present invention is appropriately determined, taking into account conditions, body weight, age, sex, etc. of the patient. It usually ranges from 0.1 to 10 mg/day for intravenous administration and from 0.5 to 50 mg/day for oral administration for adult in a single or several divided doses.

The pharmacological effects of the compounds of the present invention were confirmed by Test Examples.

TEST EXAMPLE 1

Antagonism Against 5-$HT_3$-Receptor

Nine-week-old Wistar male rats were anesthetized by intraperitoneal administration of 1 g/kg of urethane, and blood pressure and heart rate were measured under artificial respiration. Transient reduction in heart rate and blood pressure induced by intravenous administration of serotonin or 2-methylserotonin which is a selective agonist of 5-$HT_3$ was taken as an index of the reaction via 5-$HT_3$ receptor [Bezold-Jarish reflex; Paintal, A. S., *Pysiolo. Rev.*, Vol. 53, p. 159 (1973)].

When the compound of the present invention or a salt thereof was intravenously administered (0.03 to 3 $\mu$g/kg) or orally administered (1 to 30 $\mu$g/kg) 10 minutes or 60 minutes before the administration of serotonin (or 2-methylserotonin), respectively, the reduction in heart rate and blood pressure induced by serotonin or 2-methylserotonine was dose-dependently inhibited.

Inhibitory activity of the compound of the present invention on serotonin-induced Bezold-Jarish (BJ) reflex in rats is shown in Table 1 below.

TABLE 1

| Example No. of Test Compound | BJ Reflex Inhibitory Activity $ED_{50}$; $\mu$g/kg, i.v.) |
|---|---|
| 2 | 0.29 |
| 4 | 0.044 |
| 9 | 0.80 |

| Example No. of Test Compound | BJ Reflex Inhibitory Activity ED$_{50}$; μg/kg, i.v.) |
| --- | --- |
| 36 | 0.063 |

TEST EXAMPLE 2

Inhibition on Anticancer Agent-Induced Vomiting

When male ferrets weighing from 1 to 1.5 kg subcutaneously or orally received 0.01 to 0.3 mg/kg of the compound of the present invention, vomiting induced by intraperitoneal administration of 10 mg/kg of Cisplatin was inhibited.

TEST EXAMPLE 3

Inhibition on Stress Defecation

Nine-week-old male Wistar rats were encased in a cage for restricted stress, and the number of feces was measured. Intravenous administration of the compound of the present invention or a salt thereof (1 to 100 μg/kg) dose-dependently inhibited acceleration of defecation induced by restricted stress.

TEST EXAMPLE 4

Toxicity

Acute toxicity of the compounds of the present invention in male mice was from 100 to 150 mg/kg i.v. as determined by an up-and-down method, indicating that the compounds are of low toxicity.

The present invention is now illustrated in greater detail with reference to Reference Examples, Examples, and Formulation Examples, but it should be understood that the present invention is not deemed to be limited thereto.

REFERENCE EXAMPLE 1

(a) 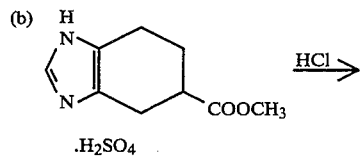

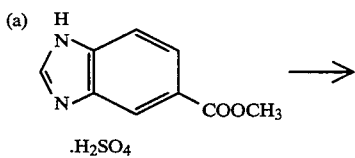

In 600 ml of acetic acid was dissolved 40.0 g of methyl 5-benzimidazole carboxylate sulfate in a 1 l-volume autoclave, and 11 g of 10% palladium-on-carbon was added to the solution as a catalyst to conduct hydrogenation at 80° C. at a pressure of 60 atm for 5 hours. The catalyst was separated by filtration, and the mother liquor was concentrated under reduced pressure to obtain 41.0 g of methyl 4,5,6,7-tetrahydrobenzimidazole-5-carboxylate sulfate as an oil.

(b) 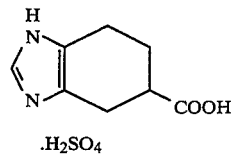

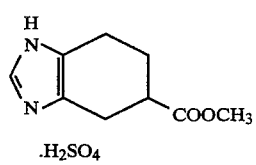

In a mixture of 350 ml of water and 340 ml of concentrated hydrochloric acid was dissolved 41.0 g of the oily ester sulfate as obtained in (a) above, and the mixture was stirred at 100° C. for 3 hours. After concentration, the resulting crystal was washed with acetone to obtain 29.6 g (76.8% based on the benzimidazole ester) of 4,5,6,7-tetrahydrobenzimidazole-5-carboxylic acid sulfate.

Physicochemical Properties:
Melting Point: 145°–148° C.
NMR (d$_6$-DMSO): δ 1.60–3.00 (7H, m), 8.84 (1H, s)
Mass Spectrum (EI): m/z; 166 (M$^+$, as a free compound) (CI): m/z; 167 (M$^+$+1, as a free compound)

REFERENCE EXAMPLE 2

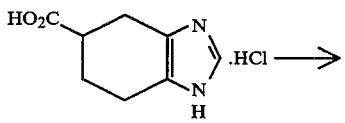

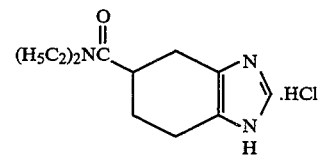

To 0.30 g of 4,5,6,7-tetrahydrobenzimidazole-5-carboxylic acid hydrochloride containing sodium chloride was added 5 ml of thionyl chloride, followed by stirring at 90° C. for 2 hours. The excess of thionyl chloride was removed by distillation under reduced pressure. To the residue was added 10 ml of dichloromethane, and 2 ml of diethylamine was added thereto at 5° C., followed by stirring at room temperature for 16 hours. To the mixture was added 40 ml of dichloromethane, and the mixture was washed with a saturated aqueous solution of sodium hydrogencarbonate and dried over anhydrous magnesium sulfate. The solvent was removed by distillation under reduced pressure to obtain 0.22 g of N,N-diethyl-4,5,6,7-tetrahydrobenzimidazole-5-carboxamide.

Physicochemical Properties:
NMR (TMS, CDCl$_3$): δ 1.15 (t, 6H), 2.0–3.5 (m, 7H), 3.10 (q, 4H), 8.15 (s, 1H), 9.50 (s, 1H)
Mass Spectrum (FAB, Pos) m/z; 222 (M$^+$+1)

To the above obtained compound was added 1 ml of a 4N solution of hydrogen chloride in ethyl acetate, and the solvent was removed by distillation under reduced pressure to obtain 0.27 g of N,N-diethyl-4,5,6,7-tetrahydrobenzimidazole-5-carboxamide hydrochloride.

EXAMPLE 1

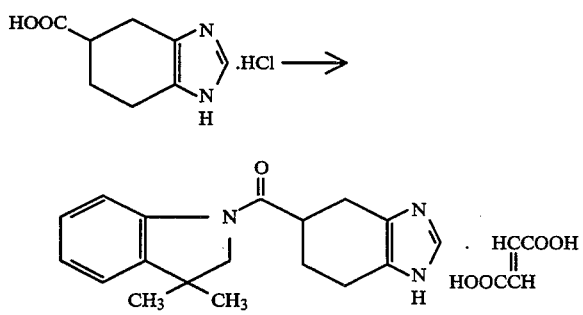

In 0.7 ml of thionyl chloride, 0.13 g of 4,5,6,7-tetrahydrobenzimidazole-5-carboxylic acid hydrochloride (containing sodium chloride) was refluxed for 30 minutes, and volatile components were removed by distillation under reduced pressure. The residue was added to a solution of 0.15 g of 3,3-dimethylindoline and 0.15 ml of triethylamine in 2 ml of dichloromethane under ice-cooling. After stirring the mixture at room temperature overnight, 5 ml of a sodium carbonate aqueous solution was added thereto, and the mixture was extracted with chloroform. The organic layer was dried, and the solvent was removed by distillation under reduced pressure. The residue was subjected to silica gel column chromatography using chloroform/methanol as an eluent to obtain 0.11 g of 5-[(2,3-dihydro-3,3-dimethylindol-1-yl)carbonyl]-4,5,6,7-tetrahydrobenzimidazole as an oily substance. The oily substance was then treated with a solution of fumaric acid in methanol/acetonitrile to obtain 0.09 g of 5-[(2,3-dihydro-3,3-dimethylindol-1-yl)carbonyl]-4,5,6,7-tetrahydrobenzimidazole fumarate.

Physicochemical Properties:

Melting Point: 119°–123° C.

Elemental Analysis for $C_{18}H_{21}N_3O \cdot C_4H_4O_4 \cdot H_2O \cdot 0.3CH_3CN$: Calcd. (%): C 61.44; H 6.36; N 10.46 Found (%): C 61.60; H 6.03; N 10.46

Mass Spectrum (EI): m/z; 295 (M+, as a free compound)

In the same manner as in Example 1, the following compounds were synthesized.

EXAMPLE 2

5-[(2,3-Dihydroindol-1-yl)carbonyl]-4,5,6,7-tetrahydrobenzimidazole fumarate

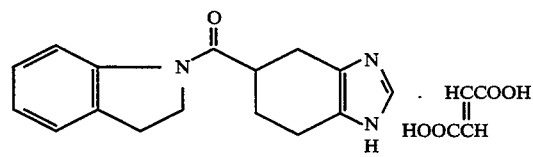

Physicochemical Properties:

Melting Point: 206°–208° C. (methanol/acetonitrile)

Elemental Analysis for $C_{16}H_{17}N_3O \cdot C_4H_4O_4 \cdot 0.3H_2O$: Calcd. (%): C 61.78; H 5.60; N 10.81 Found (%): C 61.92; H 5.53; N 10.68

Mass Spectrum (EI): m/z; 267 (M+, as a free compound)

EXAMPLE 3

5-[(2-Methyl-2,3-dihydroindol-1-yl)carbonyl]-4,5,6,7-tetrahydrobenzimidazole

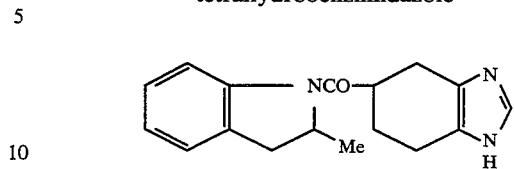

Physicochemical Properties:

Melting Point: 230°–234° C. (dec.) (recrystallized from ethyl acetate/hexane)

Elemental Analysis for $C_{17}H_{19}N_3O$: Calcd. (%): C 72.57; H 6.81; N 14.93 Found (%): C 72.76; H 6.78; N 14.62

Mass Spectrum: m/z; 281 (M+)

EXAMPLE 4

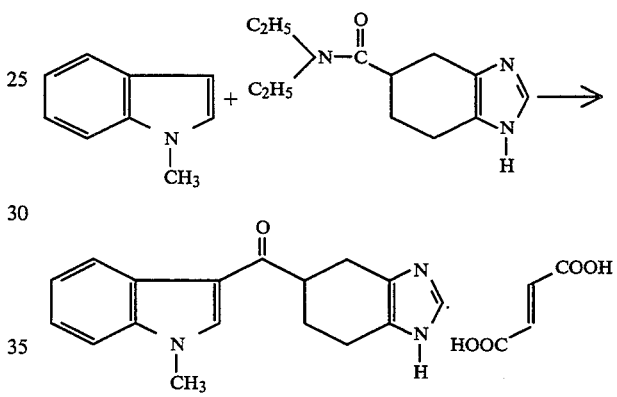

A mixture of 0.27 g (1.05 mmol) of N,N-diethyl 4,5,6,7-tetrahydrobenzimidazole-5-carboxamide hydrochloride, 0.16 ml (1.25 mmol) of 1-methylindole, and 0.15 ml (1.65 mmol) of phosphorus oxychloride was heated at 80° C. for 2 hours while stirring. 30 ml of water were added thereto, and the mixture was rendered basic with a 1N sodium hydroxide aqueous solution, followed by extracting with ethyl acetate. The ethyl acetate layer was dried over anhydrous magnesium sulfate and filtered. The filtrate was distilled under reduced pressure, and the residue was purified by silica gel column chromatography (eluent: dichloromethane/methanol/aqueous ammonia=10:1:0.1 by volume) and preparative thin layer chromatography (developing solvent: dichloromethane/methanol/aqueous ammonia=10:1:0.1 by volume) to obtain 20 mg of a foaming substance. To the product was added 10 mg of fumaric acid to convert it to a fumarate. Recrystallization from ethyl acetate/methanol (10:1 by volume) gave 10 mg of 5-[(1-methylindol-3-yl)carbonyl]-4,5,6,7-tetrahydrobenzimidazole fumarate.

Physicochemical Properties:

Melting Point: 97°–102° C.

Mass Spectrum (EI): m/z; 279 (M+, as a free compound)

NMR (CDCl₃) δ (as a free compound):

1.90–3.00 (7H, m, CH₂, CH), 3.80 (3H, s, N-Me), 7.20 (2H, m, ArH), 7.50–8.00 (4H, m, ArH), 8.30 (1H, m, NH)

EXAMPLE 5

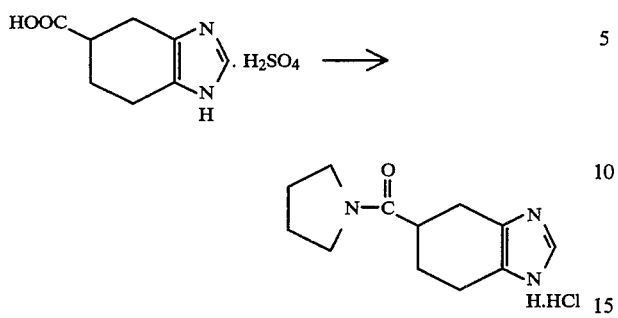

In 53 ml of acetonitrile were added 5.3 g of 4,5,6,7-tetrahydrobenzimidazole-5-carboxylic acid sulfate and 2.9 ml of thionyl chloride, and the mixture was stirred at 53° to 55° C. for 1.5 hours. The mixture was distilled under reduced pressure to remove 10 to 15 ml of the solvent. After 15 ml of acetonitrile was added thereto, the mixture was further distilled under reduced pressure to remove 10 to 15 ml of the solvent. The residual solution was added dropwise to a solution of 14.2 g of pyrrolidine in 50 ml of acetonitrile at 2° C. or lower. After the addition, the temperature was returned to room temperature, and the mixture was stirred for 1 hour, followed by concentration under reduced pressure. To the residue was added 30 ml of a saturated sodium chloride aqueous solution, and the mixture was extracted with chloroform (50 ml×3). The chloroform layer was dried over anhydrous magnesium sulfate, concentrated under reduced pressure, treated with hydrochloric acid in ethanol, and recrystallized from ethanol/ethyl acetate to obtain 4.25 g (82.9%) of N-[(4,5,6,7-tetrahydrobenzimidazol-5-yl)carbonyl]pyrrolidine hydrochloride.

Physicochemical Properties:
Melting Point: 234°–236° C.
Elemental Analysis for $C_{12}H_{18}N_3OCl.0.2H_2O$: Calcd. (%): C 55.57; H 7.15; N 16.20; Cl 13.67 Found (%): C 55.64; H 6.99; N 16.18; Cl 13.79
Mass Spectrum (EI): m/z; 291 ($M^+$, as a free compound)

In the same manner as in Example 5, the following compounds were synthesized.

EXAMPLE 6

4-(4,5,6,7-Tetrahydrobenzimidazol-5-ylcarbonyl)-2,3-dihydro-1,4-benzoxazine fumarate

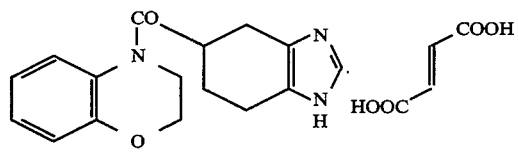

Physicochemical Properties:
Melting Point: 176°–178° C. (methanol/acetonitrile)
Mass Spectrum (EI): m/z; 283 ($M^+$, as a free compound)
Elemental Analysis for $C_6H_7N_3O_2.C_4H_4O_4$: Calcd. (%): C 60.14; H 5.30; N 10.52 Found (%): C 59.95; H 5.28; N 10.55

EXAMPLE 7

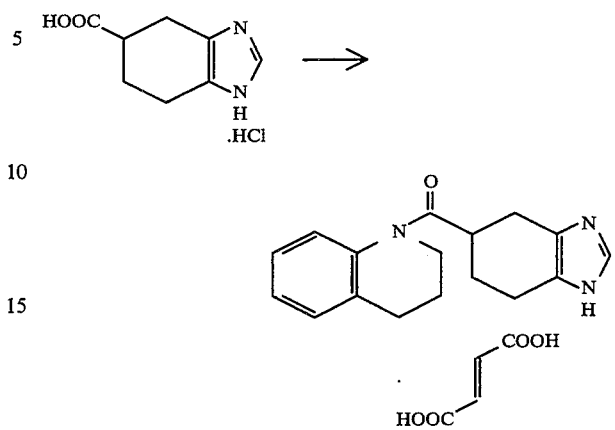

In 5 ml of thionyl chloride was added 0.58 g (0.98 mmol) of 4,5,6,7-tetrahydrobenzimidazole-5-carboxylic acid hydrochloride having a purity of 34.5% (containing sodium chloride), and the mixture was stirred at 90° C. for 4 hours. After cooling, the solution was distilled under reduced pressure to remove thionyl chloride. To the residue was added 10 ml of dichloromethane, and 0.20 ml (1.59 mmol) of 1,2,3,4-tetrahydroquinoline and 0.35 ml (2.53 mmol) of triethylamine were added thereto, followed by stirring at room temperature for 48 hours. To the reaction mixture was added 40 ml of dichloromethane, and the mixture was washed with a 1N sodium hydroxide aqueous solution and dried over anhydrous magnesium sulfate. The solvent was removed by distillation under reduced pressure, and the residue was subjected to silica gel column chromatography using dichloromethane/methanol/aqueous ammonia (10:1:0.1 by volume) as an eluent to obtain 100 mg of a foam-like substance, which was then treated with 40 mg of fumaric acid in ethanol to be converted to a fumarate. Recrystallization from ethyl acetate/methanol (10:1 by volume) gave 90 mg (33.3%) of 1-[(4,5,6,7-tetrahydrobenzimidazol-5-yl)carbonyl]-1,2,3,4-tetrahydroquinoline fumarate.

Physicochemical Properties:
Melting Point: 98°–100° C.
Elemental Analysis for $C_{17}H_{19}N_3O.C_4H_4O_4.2H_2O$: Calcd. (%): C 58.19; H 6.27; N 9.69 Found (%): C 58.43; H 5.73; N 9.53
NMR (DMSO-$d_6$) δ ppm: 1.90 (4H, q, 7 Hz, quinoline $CH_2\times2$), 2.00–3.00 (7H, m, benzimidazole $CH_2\times3$, CH), 3.70 (2H, t, J=7 Hz, $CH_2N$), 6.60 (2H, s, fumaric acid CH×2), 7.16 (5H m, ArH, NH), 7.55 (1H, s, imidazole CH)
Mass Spectrum (EI): m/z; 281 ($M^+$, as a free compound)

EXAMPLE 8

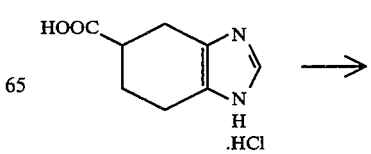

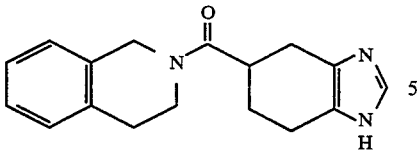

To 5 ml of thionyl chloride was added 0.58 g (0.98 mmol) of 4,5,6,7-tetrahydrobenzimidazole-5-carboxylic acid hydrochloride having a purity of 34.5% (containing sodium chloride), followed by stirring at 90° C. for 4 hours. After cooling, the reaction mixture was distilled under reduced pressure to remove thionyl chloride. To the residue were added 10 ml of dichloromethane, 0.20 ml (1.57 mmol) of 1,2,3,4-tetrahydroisoquinoline, and 0.35 ml (2.53 mmol) of triethylamine, and the mixture was stirred at room temperature for 48 hours. To the reaction mixture was added 40 ml of dichloromethane, and the mixture was washed with a 1N sodium hydroxide aqueous solution and dried over anhydrous magnesium sulfate. The solvent was removed from the residue by distillation under reduced pressure. The residue was subjected to silica gel column chromatography using dichloromethane/methanol/aqueous ammonia (10:1:0.1 by volume) as an eluent to obtain 0.15 g of a white foam-like substance, which was then recrystallized from diethyl ether/ethyl acetate to obtain 40 mg (14.8%) of 2-[(4,5,6,7-tetrahydrobenzimidazol-5-yl)carbonyl]-1,2,3,4-tetrahydroisoquinoline.

Physicochemical Properties:

Melting Point: 128°–130° C.

NMR (DMSO-d$_6$) δ ppm: 2.00–3.00 (7H, m, CH$_2$×3, CH, benzimidazole), 3.00 (2H, t, J=5 Hz, CH$_2$), 3.40 (2H, t, J=5 Hz, —CH$_2$—), 4.24 (2H, s, CH$_2$N), 7.22 (6H, m, ArH, NH)

Mass Spectrum (EI): m/z; 281 (M$^+$)

EXAMPLE 9

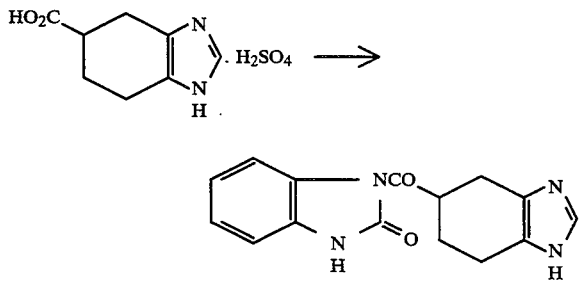

A mixture of 0.78 g of 4,5,6,7-tetrahydrobenzimidazole-5-carboxylic acid sulfate and 3 ml of thionyl chloride was heated at 50° C. for 20 minutes, and the excess of thionyl chloride was removed by concentration under reduced pressure to obtain a carboxylic acid chloride. A solution of the resulting carboxylic acid chloride in 3 ml of dimethylformamide was added to a dimethylformamide solution (30 ml) of 1.61 g of 2-hydroxybenzimidazole and 0.50 g of 60% oily sodium hydride under ice-cooling, and the reaction mixture was stirred at room temperature for 1 hour, followed by concentration under reduced pressure. The residue was made acidic with 0.5N hydrochloric acid, and any insoluble matter was removed by filtration. The filtrate was made basic with potassium carbonate, and the thus formed crystal was collected by filtration, washed with water, and stirred in acetone overnight. The resulting crystal was collected by filtration to yield 0.20 g (24%) of 1-[(4,5,6,7-tetrahydrobenzimidazol-5-yl)carbonyl]-2,3-dihydrobenzimidazol-2-one.

Physicochemical Properties:

Melting Point: 271°–274° C. (dec.)

Elemental Analysis for C$_{15}$H$_{14}$N$_4$O$_2$.0.4H$_2$O: Calcd. (%): C 62.23; H 5.15; N 19.35 Found (%): C 62.41; H 5.02; N 19.06

Mass Spectrum (EI): m/z; 282 (M$^+$)

In the same manner as in Example 9, the following compounds were synthesized.

EXAMPLE 10

5-Methoxy-1-[(4,5,6,7-tetrahydrobenzimidazol-5-yl)carbonyl]-2,3-dihydrobenzimidazol-2-one fumarate

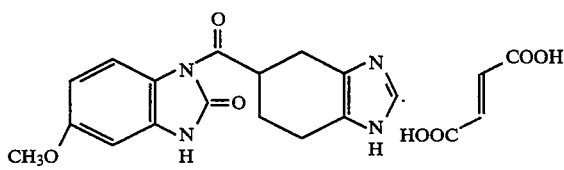

Physicochemical Properties:

Melting Point: 215°–218° C. (dec.) (recrystallized from methanol)

Mass Spectrum (EI): m/z; 312 (M$^+$, as a free compound)

NMR (DMSO-d$_6$) δ ppm: 1.57–2.34 (2H, m), 2.34–3.10 (4H, m), 3.76 (3H, s), 3.90–4.28 (1H, m), 6.58 (2H, s), 6.32–6.84 (2H, m), 7.62 (1H, s), 7.89 (1H, d, J=8 Hz)

EXAMPLE 11

1-Methyl-3-[(4,5,6,7-tetrahydrobenzimidazol-5-yl)carbonyl]-2,3-dihydrobenzimidazol-2-one fumarate

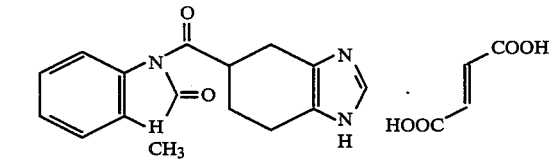

Physicochemical Properties:

Melting Point: 145°–147° C. (recrystallized from methanol/acetonitrile)

Mass Spectrum (EI): m/z; 296 (M$^+$, as a free compound)

Elemental Analysis for C$_{16}$H$_{16}$N$_4$O$_2$.C$_4$H$_4$O$_4$.0.5-H$_2$O): Calcd. (%): C 57.00; H 5.02; N 13.30 Found (%): C 56.91; H 5.06; N 13.31

EXAMPLE 12

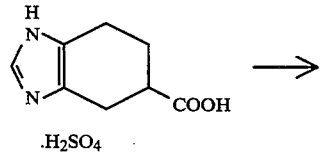

-continued

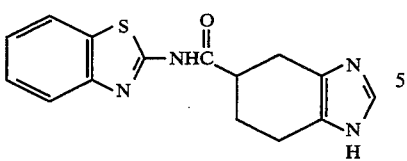

In 10 ml of 1,2-dichloroethane were heat-refluxed 1.32 g of 4,5,6,7-tetrahydrobenzimidazole-5-carboxylic acid sulfate and 1.78 g of thionyl chloride for 30 minutes. The excess of thionyl chloride and the solvent were removed by distillation under reduced pressure, and the residue was dissolved in 4.0 ml of dry dimethylformamide. The solution was added to a solution of 2.7 g of 2-aminobenzothiazole in 10 ml of dry dimethylformamide under ice-cooling, followed by stirring at room temperature for 1 hour. The solvent was removed by distillation under reduced pressure, and the residue was purified by silica gel column chromatography using a methylene chloride/methanol mixed solvent as a developing solvent followed by recrystallization from ethanol to obtain 0.8 g (53.7%) of N-(2-benzothiazolyl)-4,5,6,7-tetrahydrobenzimidazol-5-ylcarboxamide.

Physicochemical Properties:
Melting Point: 165°–167° C.
Elemental Analysis for $C_{15}H_{14}N_4OS.0.25H_2O$: Calcd. (%): C 59.49; H 4.82; N 18.50; S 10.59 Found (%): C 59.30; H 4.73; N 18.49; S 10.68
Mass Spectrum (EI): m/z; 298 (M+)

In the same manner Example 12, the following compounds were synthesized.

EXAMPLE 13

N-(2-Benzimidazolyl)-4,5,6,7-tetrahydrobenzimidazol-5-ylcarboxamide

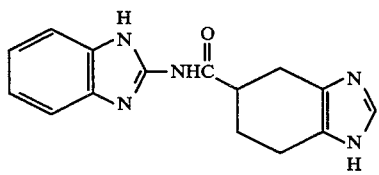

Physicochemical Properties:
Melting Point: 182°–185° C.
Elemental Analysis for $C_{15}H_{15}N_5O.0.6H_2O$: Calcd. (%): C 61.67; H 5.58; N 23.97 Found (%): C 61.63; H 5.44; N 23.97
Mass Spectrum (EI): m/z; 281 (M+)

EXAMPLE 14

N-(Quinolin-3-yl)-4,5,6,7-tetrahydrobenzimidazol-5-ylcarboxamide

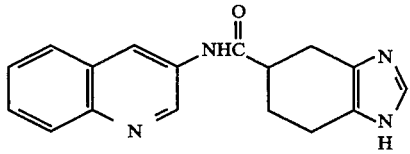

Physicochemical Properties:
Melting Point: 296°–297° C.

Elemental Analysis for $C_{17}H_{16}N_4O.0.25H_2O$: Calcd. (%): C 68.79; H 5.60; N 18.87 Found (%): C 68.69; H 5.66; N 18.75
Mass Spectrum (EI): m/z; 292 (M+)

EXAMPLE 15

N-(5-Methyl-1,3,4-thiadiazol-2-yl)-4,5,6,7-tetrahydrobenzimidazole-5-carboxamide

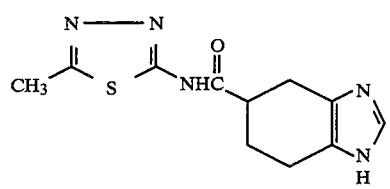

Physicochemical Properties:
Melting Point: >300° C.
Elemental Analysis for $C_{11}H_{13}N_5OS.0.2H_2O$: Calcd. (%): C 49.50; H 5.06; N 26.24; S 12.01 Found (%): C 49.86; H 4.97; N 26.40; S 11.68
Mass Spectrum (EI): m/z; 263 (M+)

EXAMPLE 16

N-(9-Ethylcarbazol-3-yl)-4,5,6,7-tetrahydrobenzimidazol-5-carboxamide

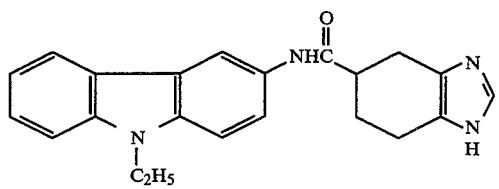

Physicochemical Properties:
Melting Point: 168°–170° C.
Elemental Analysis for $C_{22}H_{22}N_4O.0.5H_2O$: Calcd. (%): C 71.91; H 6.31; N 15.25 Found (%): C 71.77; H 6.13; N 15.13
Mass Spectrum (EI): m/z; 358 (M+)

EXAMPLE 17

N-[(4,5,6,7-Tetrahydrobenzimidazol-5-yl)carbonyl]-phenothiazine hydrochloride

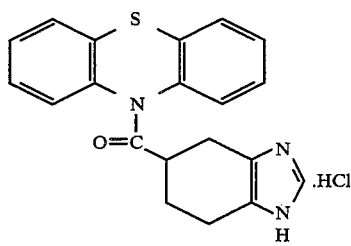

Physicochemical Properties:
Melting Point: 268°–270° C.
Elemental Analysis for $C_{20}H_{17}N_3OS.HCl.0.5H_2O$: Calcd. (%): C 61.14; H 4.87; N 10.69; Cl 19.02 Found (%): C 61.15; H 4.64; N 10.60; Cl 8.59
Mass Spectrum (EI): m/z; 347 (M+, as a free compound)

EXAMPLE 18

N-(5,6-Dihydro-4H-cyclopentathiazol-2-yl)-4,5,6,7-tetrahydrobenzimidazole-5-carboxamide

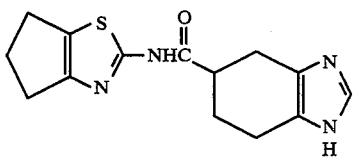

Physicochemical Properties:
Melting Point: 164°–165° C.
NMR (DMSO$_6$) δ ppm: 1.70–3.00 (13H), 7.426 (1H)
Mass Spectrum (EI): m/z; 288 (M+), 255

EXAMPLE 19

N-(Pyrimidin-2-yl)-4,5,6,7-tetrahydrobenzimidazol-5-carboxamide dihydrochloride

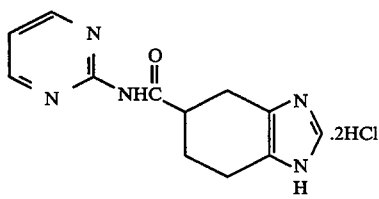

Physicochemical Properties:
Melting Point: 287°–289° C.
Elemental Analysis for $C_2H_{13}N_5O.2HCl.1.4H_2O$: Calcd. (%): C 42.22; H 5.25; N 20.51; Cl 20.77 Found (%): C 42.35; H 5.00; N 20.69; Cl 20.45
Mass Spectrum (EI): m/z; 243 (M+, as a free compound)

EXAMPLE 20

N-(Pyridin-3-yl)-4,5,6,7-tetrahydrobenzimidazole-5-carboxamide dihydrochloride

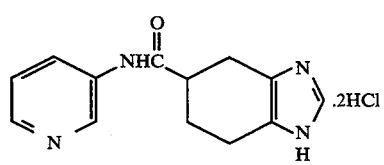

Physicochemical Properties:
Melting Point: 285°–287° C.
Elemental Analysis for $C_{13}H_{14}N_4O.2HCl$: Calcd. (%): C 49.54; H 5.12; N 17.77 Found (%): C 49.74; H 5.26; N 17.53
Mass Spectrum (EI): m/z; 242 (M+, as a free compound)

EXAMPLE 21

N-(3-Ethoxycarbonyl-4,5,6,7-tetrahydrobenzo]b]thiophen-2-yl)-4,5,6,7-tetrahydrobenzimidazole-5-carboxamide

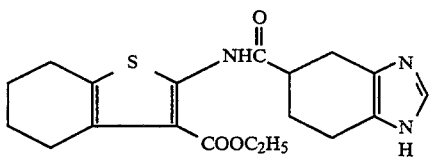

Physicochemical Properties:
Melting Point: 159°–161° C.
Elemental Analysis for $C_{19}H_{23}N_3O_3S$: Calcd. (%): C 61.10; H 6.21; N 11.25; S 8.59 Found (%): C 60.87; H 6.16; N 11.05; S 8.62
Mass Spectrum (EI): m/z; 373 (M+)

EXAMPLE 22

N-(Indazol-6-yl)-4,5,6,7-tetrahydrobenzimidazole-5-carboxamide

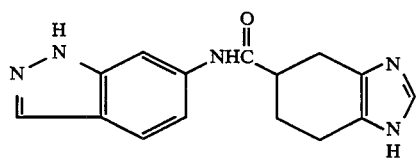

Physicochemical Properties:
Melting Point: >300° C.
Elemental Analysis for $C_{15}H_{15}N_5O$: Calcd. (%): C 64.04; H 5.37; N 24.89 Found (%): C 63.79; H 5.42; N 24.75
Mass Spectrum (EI): m/z; 281 (M+)

EXAMPLE 23

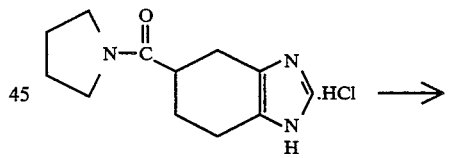

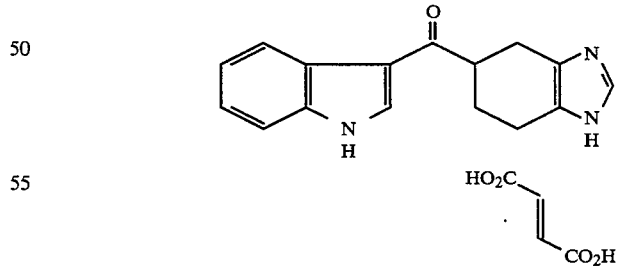

4 g of N-[(4,5,6,7-tetrahydrobenzimidazol-5-yl)carbonyl]pyrrolidine hydrochloride obtained in Example 5 were added to 40 ml of dichloroethane, and 2.74 g of indole and 4.4 ml of phosphorus oxychloride were added thereto. The mixture was stirred at 80° to 85° C. for 7 hours and then at room temperature overnight. To the mixture was added 40 ml of a cold potassium carbonate aqueous solution, followed by extraction with chloroform. The extract was dried over anhydrous magnesium sulfate, and the solvent was removed by distillation under reduced pressure. The residue was subjected to column chromatography using chloroform/methanol as an eluent to obtain 1.82 g of 5-[(indol-3-yl)carbonyl]-4,5,6,7-tetrahydrobenzimidazole as a foam-like substance. In 1 ml of methanol were dissolved 0.16 g of the resulting product and 0.06 g of fumaric acid, and 5 ml of acetonitrile was added to the solution. The formed crystal was collected by filtration to obtain 0.13 g of 5-[(indol-3-yl)carbonyl]-4,5,6,7-tetrahydrobenzimidazole fumarate.

Physicochemical Properties:
Melting Point: 153°–154° C.
Elemental Analysis for $C_{16}H_{15}N_3O \cdot C_4H_4O_4 \cdot 0.15CH_3CN \cdot 0.65H_2O$: Calcd. (%): C 61.07; H 5.24; N 11.05 Found (%): C 61.11; H 5.01; N 11.04
Mass Spectrum (FAB): m/z; 266 (M+ +1, as a free compound)

In the same manner as in Example 23, the following compounds were synthesized.

EXAMPLE 24

5-[(1,2-Dimethylindol-3-yl)carbonyl]-4,5,6,7-tetrahydrobenzimidazole ¾ fumarate

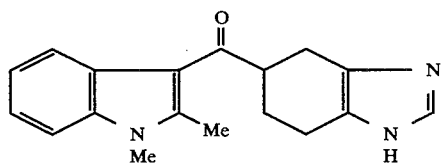

Physicochemical Properties:
Melting Point: 220°–223° C.
Elemental Analysis for $C_{18}H_{19}N_3O \cdot \tfrac{3}{4}C_4H_4O_4$: Calcd. (%): C 66.30; H 5.83; N 11.05 Found (%): C 66.50; H 5.83; N 11.13

Mass Spectrum (EI): m/z; 293 (M+, as a free compound)

EXAMPLE 25

5-[(2-Methylindol-3-yl)carbonyl]-4,5,6,7-tetrahydrobenzimidazole ½ fumarate

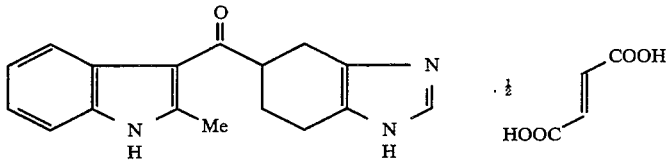

Physicochemical Properties:
Melting Point: 221°–223° C.
Elemental Analysis for $C_{17}H_{17}N_3O \cdot \tfrac{1}{2}C_4H_4O_4 \cdot 0.25H_2O$: Calcd. (%): C 66.75; H 5.75; N 12.29 Found (%): C 66.73; H 5.75; N 12.29
Mass Spectrum (EI): m/z; 279 (M+, as a free compound)

EXAMPLE 26

5-[(2-Benzylindol-3-yl)-carbonyl]-4,5,6,7-tetrahydrobenzimidazole fumarate

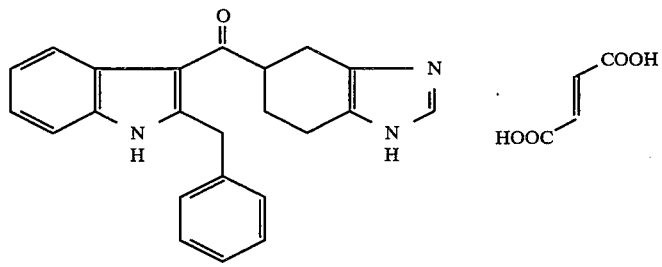

Physicochemical Properties:
Melting Point: 183°–186° C.
Elemental Analysis for $C_{23}H_{21}N_3O \cdot C_4H_4O_4 \cdot 0.1H_2O$: Calcd. (%): C 68.52; H 5.37; N 8.88 Found (%): C 68.38; H 5.50; N 8.87
Mass Spectrum (EI): m/z; 355 (M+, as a free compound)

EXAMPLE 27

5-[(5-Methoxyindol-3-yl)carbonyl]-4,5,6,7-tetrahydrobenzimidazole ¾ fumarate

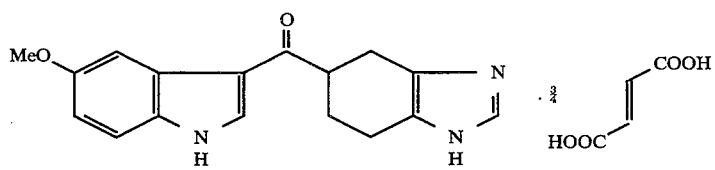

Physicochemical Properties:
Melting Point: 162°–164° C.

Elemental Analysis for $C_{17}H_{17}N_3O_2 \cdot \frac{3}{4}C_4H_4O_4 \cdot 0.2CH_3CN \cdot 0.85H_2O$: Calcd. (%): C 60.36; H 5.54; N 11.04 Found (%): C 60.33; H 5.25; N 10.93

Mass Spectrum (EI): m/z; 295 (M+, as a free compound)

EXAMPLE 28

5-[(5-Chloro-2-methylindol-3-yl)-carbonyl]-4,5,6,7-tetrahydrobenzimidazole fumarate

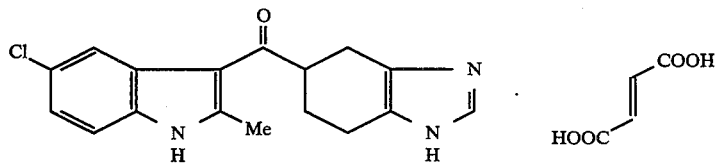

Physicochemical Properties:
Melting Point: 212°–213° C.
Elemental Analysis for $C_{17}H_{16}N_3OCl \cdot C_4H_4O_4$: Calcd. (%): C 58.68; H 4.67; N 9.78; Cl 8.25 Found (%): C 58.43; H 4.91; N 9.67; Cl 18.24

Mass Spectrum (FAB, Pos): m/z; 314 (M++1, as a free compound)

EXAMPLE 29

5-[(5-Nitroindol-3-yl)carbonyl]-4,5,6,7-tetrahydrobenzimidazole

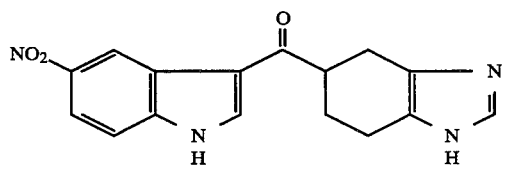

Physicochemical Properties:
Melting Point: 227°–229° C.
NMR (DMSO-$d_6$) 100M, δ: 2.00 (2H, m), 2.70 (4H, m), 3.63 (1H, m), 7.44 (1H, s), 7.64 (1H, d, $J_{6.7}$=12 Hz), 8.10 (1H, dd, $J_{6.7}$=12 Hz, $J_{4.6}$=4 Hz), 8.72 (1H, s), 9.07 (1H, d, $J_{4.6}$=4 Hz), 12.56 (1H, br)

Mass Spectrum (EI): m/z; 310 (M+)

EXAMPLE 30

5-[(5-Methoxycarbonylindol-3-yl)-carbonyl]-4,5,6,7-tetrahydrobenzimidazole

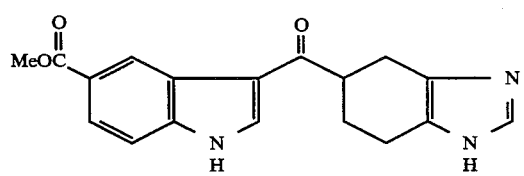

Physicochemical Properties:
Melting Point: 205°–209° C.
NMR (DMSO-$d_6$) 100M δ: 1.90–2.15 (2H, m), 2.83 (4H, br), 3.75 (1H, br), 7.56 (1H, d, $J_{6.7}$=12 Hz), 7.84 (1H, dd, $J_{6.7}$=12 Hz, $J_{4.6}$=3 Hz), 8.62 (1H, d, $J_{2.NH}$=4 Hz), 8.90 (2H, s), 12.60 (1H, d, $J_{2.NH}$=4 Hz)

Mass Spectrum (EI): m/z; 323 (M+)

EXAMPLE 31

5-[(5-Hydroxyindol-3-yl)carbonyl]-4,5,6,7-tetrahydrobenzimidazole ½fumarate

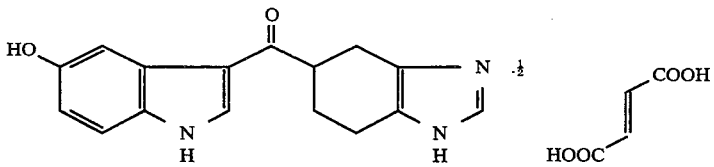

Physicochemical Properties:
Melting Point: 282°–286° C.

NMR (DMSO-$d_6$) 100M δ: 1.90 (2H, br), 2.85 (4H, br), 3.74 (1H, br), 6.76 (1H, s), 6.84 (1H, dd, $J_{6.7}$=12 Hz, $J_{4.6}$=4 Hz), 7.41 (1H, d, $J_{6.7}$=12 Hz), 7.74 (1H, d, $J_{4.6}$=4 Hz), 8.50 (1H, d, $J_{2.NH}$=5 Hz), 9.07 (1H, s), 11.95 (1H, d, $J_{2.NH}$)

Mass Spectrum (EI): m/z; 281 (M+, as a free compound)

EXAMPLE 32

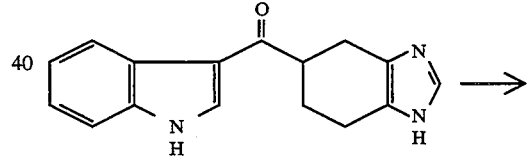

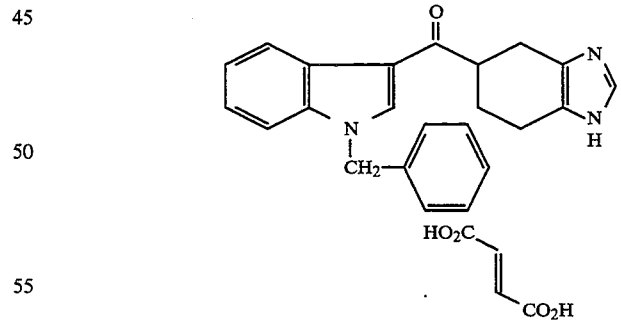

In 5 ml of dry dimethylformamide was added 0.04 g of 60% oily sodium hydride, and 0.51 g of 5-[(indol-3-yl)carbonyl]-4,5,6,7-tetrahydro-1H-benzimidazole as obtained in Example 23 was slowly added thereto at room temperature. Thirty minutes later, 0.07 g of benzyl bromide was slowly added thereto at 0° C., followed by stirring at room temperature overnight. To the reaction mixture were added 20 ml of water and 20 ml of chloroform for liquid-liquid separation. The organic layer was washed with water and dried over anhydrous magnesium sulfate. The solvent was removed by distillation, and the residue was subjected to chromatography using chloroform/methanol as an eluent. The resulting foam-like substance (0.12 g) was recrystallized together with 0.04 g of fumaric acid from ethanol/ethyl acetate to obtain 0.10 g of 5-[1-benzylindol-3-yl)carbonyl]-4,5,6,7-tetrahydrobenzimidazole fumarate.

Physicochemical Properties:
Melting Point: 117°–118° C.
Elemental Analysis for $C_{23}H_{21}N_3O \cdot C_4H_4O_4 \cdot 0.75H_2O$: Calcd. (%): C 66.86; H 5.51; N 8.66 Found (%): C 66.83; H 5.48; N 8.88
Mass Spectrum (EI): m/z; 321 (M+, as a free compound)

In the same manner as in Example 32, the following compounds were synthesized.

EXAMPLE 33

5-[(1-Cyclohexylmethylindol-3-yl)carbonyl]-4,5,6,7-tetrahydrobenzimidazole fumarate

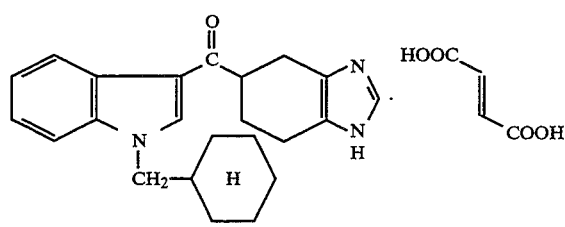

Physicochemical Properties:
Melting Point: 95°–100° C. (ethanol/ethyl acetate)
Elemental Analysis for $C_{23}H_{27}N_3O \cdot C_4H_4O_4 \cdot 0.5AcOEt$: Calcd. (%): C 62.46; H 7.05; N 7.54 Found (%): C 62.59; H 6.69; N 7.19
Mass Spectrum (EI): m/z;; 361 (M+, as a free compound)

EXAMPLE 34

5-[( 1-Allylindol-3-yl )carbonyl]-4,5,6,7-tetrahydrobenzimidazole fumarate

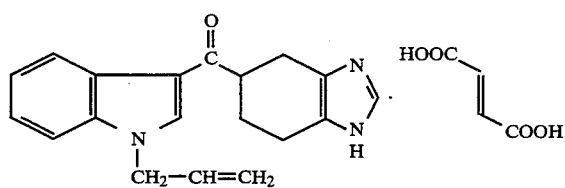

Physicochemical Properties:
Melting Point: 144°–145° C. (methanol/ethyl acetate)
Elemental Analysis for $C_{19}H_{19}N_3O \cdot C_4H_4O_4 \cdot 0.35AcOEt \cdot 0.3H_2O$: Cacld. (%): C 64.03; H 5.81; N 9.18 Found (%): C 64.00; H 5.74; N 9.17
Mass Spectrum (EI): m/z; 305 (M+, as a free compound)

EXAMPLE 35

5-[(1-n-Butylindol-3-yl)carbonyl]-4,5,6,7-tetrahydrobenzimidazole fumarate

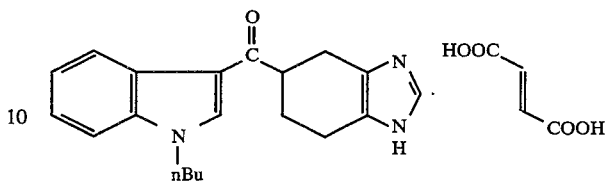

Physicochemical Properties:
Melting Point: 104°–106° C. (ethanol/acetonitrile)
Elemental Analysis for $C_{20}H_{23}N_3O \cdot C_4H_4O_4 \cdot 0.8H_2O$: Calcd. (%): C 63.78; H 6.38; N 9.30 Found (%): C 63.82; H 6.14; N 9.33
Mass Spectrum (EI): m/z; 321 (M+, as a free compound)

EXAMPLE 36

5-[[1-(2-Propynyl)indol-3-yl]carbonyl]-4,5,6,7-tetrahydrobenzimidazole fumarate

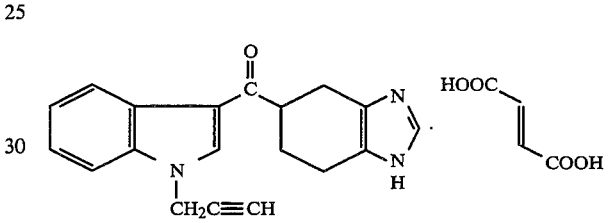

Physicochemical Properties:
Melting Point: 130°–131° C. (ethanol/acetonitrile)
Elemental Analysis for $C_{19}H_{17}N_3O \cdot C_4H_4O_4 \cdot 1.3H_2O$: Calcd. (%): C 62.38; H 5.37; N 9.49 Found (%): C 62.38; H 5.19; N 9.21
Mass Spectrum (EI): m/z; 303 (M+, as a free compound)

EXAMPLE 37

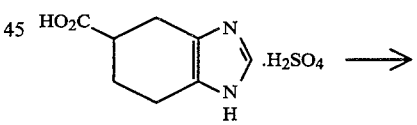

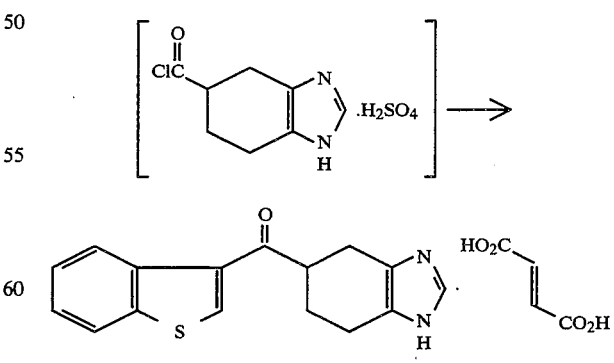

In 5 ml of acetonitrile was suspended 0.53 g of 4,5,6,7-tetrahydrobenzimidazole-5-carboxylic acid sulfate, and 0.29 ml of thionyl chloride was added to the suspension. The suspension was stirred at 55° to 60° C. for 1 hour, and the solvent was removed by distillation under reduced pressure. To the residue was added 4.6 ml of benzothiophene, and 0.4 g of aluminum chloride was then added thereto. After stirring at 60° C. for 3 hours, the reaction mixture was poured into a cold potassium carbonate aqueous solution. The solution was adjusted to a pH of 8 to 9 and extracted with chloroform. The organic layer was dried over anhydrous magnesium sulfate, and the solvent was removed by distillation. The residue was purified by silica gel column chromatography using chloroform/methanol as an eluent to obtain 5-[(benzothiophen-3yl)carbonyl]-4,5,6,7-tetrahydrobenzimidazole. The product was treated with an equimolar amount of fumaric acid in a usual manner and recrystallized from ethanol/acetonitrile to obtain 0.04 g of 5-[(benzothiophen-3-yl)carbonyl]-4,5,6,7-tetrahydrobenzimidazole fumarate.

Physicochemical Properties:
Melting Point: 135°–137° C.
Elemental Analysis for C$_{16}$H$_{14}$N$_2$OS.C$_4$H$_4$O$_4$.0.3EtOH.0.2H$_2$O): Cacld. (%): C 59.50; H 4.90; N 6.74; S 7.71 Found (%): C 59.41; H 5.07; N 6.53; S 7.91
Mass Spectrum (EI): m/z; 282 (M+, as a free compound)

EXAMPLE 38

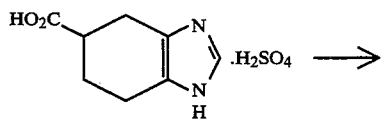

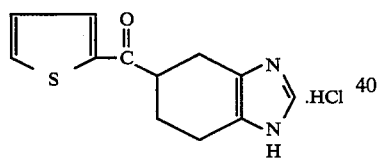

A mixture of 2 g of polyphosphoric acid, 5 ml of thiophene, and 2.91 g of 4,5,6,7-tetrahydrobenzimidazole-5-carboxylic acid sulfate was stirred at 100° C. for 8 hours. After cooling, 20 ml of cold water was added thereto, and the reaction mixture was washed with toluene (20 ml×2). The aqueous layer was adjusted to a pH of 8 to 9 with potassium carbonate and extracted from chloroform. The organic layer was dried over anhydrous magnesium sulfate, and the solvent was removed by distillation. The residue was treated with a 4N solution of hydrogen chloride in ethyl acetate and then recrystallized from methanol/acetonitrile to obtain 0.12 g of 5-[(thiophen-2-yl)carbonyl]-4,5,6,7-tetrahydrobenzimidazole hydrochloride.

Physicochemical Properties:
Melting Point: 218°–220° C.
Elemental Analysis for C$_{12}$H$_{12}$N$_2$OS.HCl: Calcd. (%): C 53.63; H 4.88; N 10.42; S 11.93 Found (%): C 53.25; H 4.98; N 10.62; S 11.70
Mass Spectrum (EI): m/z;; 232 (M+, as a free compound)

EXAMPLE 39

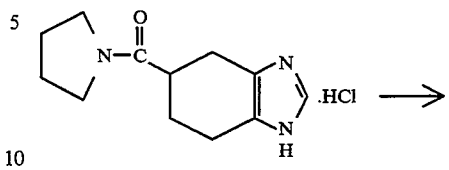

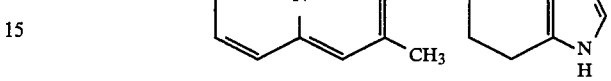

To a solution of 0.50 g of N-[(4,5,6,7-tetrahydrobenzimidazol-5-yl)carbonyl]pyrrolidinehydrochloride and 0.39 g of 2-methylindolizine in 5 ml of 1,2-dichloroethane was added dropwise 0.90 g of phosphorus oxychloride. The reaction mixture was refluxed at 85° C. for one night. After cooling to room temperature, 5 ml of water was added thereto. The organic layer was removed, and 10 ml of chloroform was added to the aqueous layer. The solution was adjusted to a pH of 9 with a 20% aqueous solution of sodium hydroxide and then extracted with chloroform. The organic layer was dried over anhydrous magnesium sulfate, and the solvent was removed by distillation. The residue was purified by silica gel column chromatography using chloroform/methanol as an eluent, followed by recrystallization from ethanol to obtain 0.21 g of 5-[(2-methylindolizin-3-yl)carbonyl]-4,5,6,7-tetrahydrobenzimidazole.

Physicochemical Properties:
Melting Point: 260°–264° C.
Elemental Analysis for C$_{17}$H$_{17}$N$_3$O.0.15C$_2$H$_5$OH.0.2H$_2$O: Calcd. (%): C 71.68; H 6.36; N 14.50 Found (%): C 71.71; H 6.16; N 14.46
Mass Spectrum (EI): m/z; 279 (M+)

EXAMPLE 40

In the same manner as in Example 39, except for replacing 2-methylindolizine with pyrrole, 5-[(2-pyrrolyl)carbonyl]-4,5,6,7-tetrahydrobenzimidazole of formula shown below was synthesized.

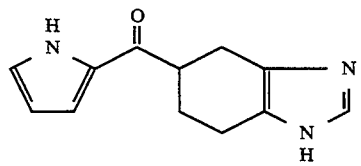

Physicochemical Properties:
Melting Point: 225°–226° C.
Elemental Analysis for C$_{12}$H$_{13}$N$_3$O: Calcd. (%): C 66.96; H 6.09; N 19.52 Found (%): C 66.74; H 6.23; N 19.41
Mass Spectrum (EI): m/z; 215 (M+)

EXAMPLE 41

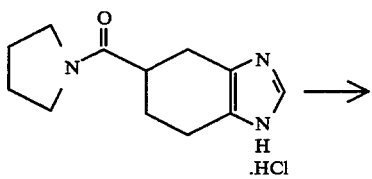

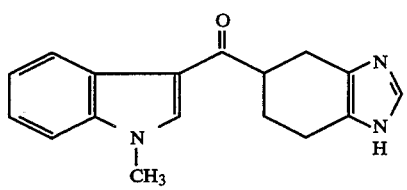

In a suspension of 7.0 g of N-[(4,5,6,7-tetrahydrobenzimidazol-5-yl)carbonyl]pyrrolidine hydrochloride and 5.4 g of N-methylindole in 70 ml of ethylene chloride was added 12.6 g of phosphorus oxychloride, and the mixture was stirred at 80° to 85° C. for 7 hours. After allowing the mixture to cool, the mixture was cooled to 0° to 5° C., and 70 ml of cold water was slowly added to the reaction mixture while maintaining the temperature of the mixture below room temperature to thereby decompose the excess of phosphorus oxychloride. The organic layer was removed, and the aqueous layer was adjusted to a pH of 9 with a 20% sodium hydroxide aqueous solution under cooling, followed by extracting from chloroform. To the chloroform layer was added 70 ml of water, and 6N hydrochloric acid was added thereto under ice-cooling while stirring to adjust to a pH of from 2.4 to 2.8. The chloroform layer was removed. The aqueous layer was washed with chloroform, and 40 ml of methanol was added thereto. The solution was made alkaline with a 20% sodium hydroxide aqueous solution while cooling. The formed crystal was collected by filtration and washed with a cold 1:1 (by volume) mixture of methanol and water to give 6.87 g (89.9%) of 5-[(1-methylindol-3-yl)carbonyl]-4,5,6,7-tetrahydrobenzimidazole.

Physicochemical Properties:
Melting Point: 139°–141° C.
Mass Spectrum (EI): m/z; 279 (M+)
1H-NMR (CDCl3-DMSO-d6): 1.80–2.32 (m, 2H), 2.56–3.04 (m, 4H), 3.32–3.60 (m, 1H), 3.90 ( s, 3H), 7.12–7.20 (m, 3H), 7.40 ( s, 1H), 7.92 (s, 1H), 8.20–8.40 (m, 1H)
Elemental Analysis for C17H17N3O.0.2EtOH.0.35H2O: Calcd. (%): 70.88; H 6.46; N 14.25 Found (%): 70.83; H 6.50; N 14.23

EXAMPLE 42

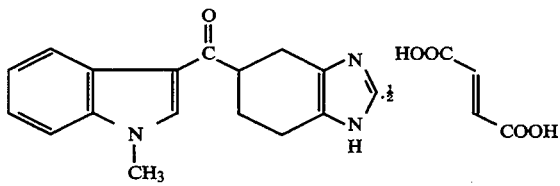

5-[(1-Methylindol-3-yl)carbonyl]-4,5,6,7-tetrahydrobenzimidazole was treated with a half molecular amount of fumaric acid in ethanol in a known manner to obtain 5-[(1-methylindol-3-yl)carbonyl]-4,5,6,7-tetrahydrobenzimidazole ½fumarate.

Physicochemical Properties:
Melting Point: 224°–225° C.
Elemental Analysis for C19H19N3O3: Calcd. (%): C 67.64; H 5.68; N 12.45 Found (%): C 67.56; H 5.66; N 12.35
Mass Spectrum (FAB): m/z; 280 (M+ +1, as a free compound)

EXAMPLE 43

Optical Resolution (1) of 5-[(1-Methylindol-3-yl carbonyl]-4,5,6,7-tetrahydrobenzimidazole (a) In 60 ml of methanol was added 5.87 g of 5-[(1-methylindol-3-yl)carbonyl]-4,5,6,7-tetrahydrobenzimidazole obtained in Example 41, and a solution of 7.52 g of (+)-dibenzoyltartaric acid in 240 ml of methanol was added thereto to once form a clear solution. On leaving the solution to stand at room temperature for one night, there were precipitated crystals, which were collected by filtration and recrystallized three times from dimethylformamide/water to obtain 2.30 g of (R)-(−)-5-[(1-methylindol-3-yl)carbonyl]-4,5,6,7-tetrahydrobenzimidazole (+)-dibenzoyltartarate.

Physicochemical Properties:
$[\alpha]_D^{20} = +30.6°$ (c=1.10, dimethylformamide)
Melting Point: 169.0°–170.0° C.
Elemental Analysis for C17H17N3O.C18H14O8.H2O: Calcd. (%): C 64.12; H 5.07; N 6.41 Found (%): C 64.13; H 5.03; N 6.55
Mass Spectrum (FAB): m/z; 280 (M+ +1, as a free compound)

(b) In a 2N hydrochloric acid aqueous solution was added 2.2 g of the compound obtained in (a) above, and the solution was washed with ethyl acetate and then adjusted to a pH of about 9 with sodium carbonate. The aqueous layer was extracted with chloroform/methanol (4:1 by volume). The extract was dried over anhydrous magnesium sulfate, and the solvent was removed by distillation to obtain 0.94 g of (R)-(−)-[(5-1-methylindol-3-yl)carbonyl]-4,5,6,7-tetrahydrobenzimidazole as a foaming substance.
$[\alpha]_D^{20} = -16.5°$ (c=1.13, methanol)

(c) (R)-(−)-5-[(1-methylindol-3-yl)carbonyl]-4,5,6,7-tetrahydrobenzimidazole (0.56 g) obtained in (b) above was treated with 0.21 g of fumaric acid in methanol/acetonitrile to obtain 0.64 g of (R)-(−)-5-[(1-methylindol-3-yl)carbonyl]-4,5,6,7-tetrahydrobenzimidazole fumarate.
$[\alpha]_D^{20} = 28.1°$ (c=1.22, methanol)
Melting Point: 150.5°–151.5° C.
Elemental Analysis for C17H17N3O.C4H4O4.0.35CH3CN.0.25H2O: Calcd. (%): C 62.91; H 5.49; N 11.33 Found (%): C 62.94; H 5.41; N 11.35
Mass Spectrum (EI): m/z; 279 (m+, as a free compound)

EXAMPLE 44

In ethanol/ethyl acetate was dissolved 100 mg of (R)-(−)-5-[(1-methyl-3-indolyl)carbonyl]-4,5,6,7-tetrahydrobenzimidazole obtained in Example 43(b), and a solution of hydrogen chloride in ethyl acetate was added thereto. The thus formed crystal was collected and recrystallized from ethanol to obtain 70 mg of (R)-(−)-5-[(1-methylindol-3-yl)carbonyl]-4,5,6,7-tetrahydrobenzimidazole hydrochloride.
$[\alpha]_D = -42.9°$ (C=1.02, methanol)

Melting Point: 215°–230° C.

Elemental Analysis for $C_{17}H_{17}N_3O \cdot HCl$: Calcd. (%): C 64.66; H 5.75; N 13.31; Cl 11.23 Found (%):C 64.37; H 5.80; N 13.12; Cl 11.17

Mass Spectrum (EI): m/z; 279 (M+, as a free compound)

EXAMPLE 45

Optical Resolution (2) of 5-[(1-methylindol-3-yl)carbonyl]-4,5,6,7-tetrahydrobenzimidazole (a) In the same manner as in Example 43(a), except for using (−)-dibenzoyltartaric acid, (S)-(+)-5-[(1-methylindol-3-yl)carbonyl]-4,5,6,7-tetrahydrobenzimidazole (−)-dibenzoyltartarate was obtained.

$[\alpha]_D^{20}$ = −30.3° (c=1.07, dimethylformamide)

Melting Point: 168.5°–169.5° C.

Elemental Analysis for $C_{17}H_{17}N_3O \cdot C_{18}H_{14}O_8 \cdot H_2O$: Calcd. (%): C 64.12; H 5.07; N 6.41 Found (%): C 64.13; H 5.13; N 6.71

Mass Spectrum (FAB): m/z; 280 (M+, +1 as a free compound.

(b) In the same manner as in Example 43(b), except for using the salt as obtained in (a) above, (S)-(+)-5-[(1-methylindol-3-yl)carbonyl]-4,5,6,7-tetrahydrobenzimidazole was obtained as a foam-like substance.

$[\alpha]_D^{20}$ = +28.3° (c=0.35, methanol)

(c) In the same manner as in Example 43(c), except for using (S)-(+)-5-[(1-methylindol-3-yl)carbonyl]-4,5,6,7-tetrahydrobenzimidazole was obtained in (b) above, a crystal of (S)-(+)-[(1-methylindol-3-yl )carbonyl]-4,5,6,7-tetrahydrobenzimidazole fumarate was obtained.

$[\alpha]_D^{20}$ = +28.3° (c=1.14, methanol)

Melting Point: 151.0°–152.0° C.

Elemental Analysis for $C_{17}H_{17}N_3O \cdot C_4H_4O_4 \cdot 0.35CH_3CN \cdot 0.25H_2O$: Calcd. (%): C 62.91; H 5.49; N 11.33 Found (%): C 62.96; H 5.39; N 11.37

Mass Spectrum (EI): m/z; 279 (M+, as a free compound)

EXAMPLE 46

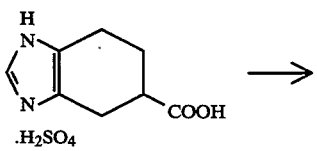

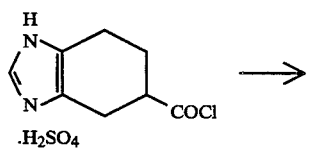

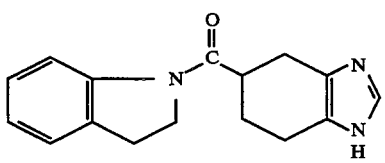

4,5,6,7-Tetrahydrobenzimidazole-5-carboxylic acid sulfate (1.32 g) was refluxed in 10 ml of 1,2-dichloroethane together with 1.78 g of thionyl chloride for 30 minutes, and the excess of thionyl chloride and the solvent were removed by distillation under reduced pressure. To the residue was added 10 ml of 1,2-dichloroethane, and 1.6 ml of indoline was added dropwise thereto at 30° C. or lower while stirring followed by stirring at room temperature for 2 hours. The reaction mixture was successively extracted once with 30 ml of water and twice with 20 ml of water. The combined aqueous layer was adjusted to a pH of 9 to 10 with a 10% sodium hydroxide aqueous solution and then extracted with methylene chloride. The combined methylene chloride layer was washed with water and dried over anhydrous magnesium sulfate. The solvent was removed by distillation under reduced pressure. The residue was recrystallized from ethyl acetate to obtain 1.1 g (82.7%) of 5-(2,3-dihydroindol-1-yl)carbonyl]-4,5,6,7-tetrahydrobenzimidazole.

Melting Point: 175°–178° C.

Mass Spectrum (EI): m/z; 267 (M+)

$^1$H-NMR (CDCl$_3$-DMSO-d$_6$): 1.80–2.36 (m, 2H), 2.48–3.12 (m, 5H), 3.24 (t, 2H), 4.20 (t, 2H), 6.84–7.30 (m, 3H), 7.50 (s, 1H), 8.20 (dd, 1H)

Elemental Analysis for $C_{16}H_{17}N_3O \cdot 0.25H_2O$: Calcd. (%): C 70.70; H 6.49; N 15.46 Found (%): C 70.79; H 6.37; N 15.19

EXAMPLE 47

5-[(2,3-Dihydroindol-1-yl)carbonyl]-4,5,6,7-tetrahydrobenz-imidazole as obtained in Example 46 was treated with hydrochloric acid in ethanol in a usual manner to obtain 5-(2,3-dihydroindol-1-yl)carbonyl]-4,5,6,7-tetrahydrobenzimidazole hydrochloride of formula:

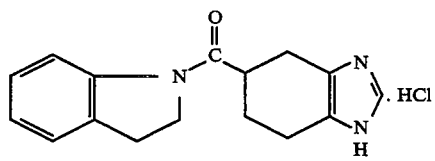

Physicochemical Properties:

Melting Point: >250° C.

Elemental Analysis for $C_{16}H_{18}N_3OCl$: Calcd. (%): C 63.26; H 5.97; N 13.83; Cl 11.67 Found (%): C 63.15; H 5.97; N 13.80; Cl 11.78

Mass Spectrum (EI): m/z; 267 (M+, as a free compound)

EXAMPLE 48

Optical Resolution (1) of 5-[(2,3-Dihydroindol-1-yl)carbonyl]-4,5,6,7-tetrahydrobenzimidazole (a) 4 g of 5-[(2,3-dihydroindol-1-yl)carbonyl]-4,5,6,7-tetrahydrobenzimidazole as obtained in Example 46 were dissolved in 50 ml of methanol, and a methanolic solution (250 ml) of 2.70 g of (−)-dibenzoyltartaric acid was added thereto. The thus formed crystal was collected by filtration, and the crystal was recrystallized twice from dimethylformamide/water to obtain 2.88 g of a (−)-dibenzoyltartarate showing optical rotation of −34.0° (20° C., sodium D-line, c=0.63 g/dl, dimethylformamide).

Physicochemical Properties:

Melting Point: 163.5°–165.0° C.

Elemental Analysis for $C_{16}H_{17}N_3O \cdot C_{18}H_{14}O_8 \cdot 0.7DMF \cdot 2.2H_2O$: Calcd. (%): C 60.59; H 5.66; N 7.22 Found (%): C 60.53; H 5.28; N 7.26

Mass Spectrum (EI): m/z; 267 (M+, as a free compound)

(b) The above prepared salt (2.65 g) was added to 2N hydrochloric acid, and the solution was washed with ethyl acetate. The solution was then adjusted to a pH of 9 with sodium carbonate. The aqueous layer was extracted with chloroform/methanol (4:1 by volume), and the extract was dried over anhydrous magnesium sulfate. The solvent was removed by distillation to obtain 0.95 g of a base showing optical rotation of $-6.3°$ (20° C., sodium D-line, c=1.05 g/dl, methanol) as a foam-like substance.

Physicochemical Properties:

Melting Point: 100°–106° C.

Elemental Analysis for $C_{16}H_{17}N_3O.0.2AcOEt.0.5-H_2O$: Calcd. (%): C 68.64; H 6.72; N 14.29 Found (%): C 68.62; H 6.53; N 14.30

Mass Spectrum (EI): m/z; 267 (M+)

(c) The above obtained foam-like base was dissolved in ethanol/ethyl acetate, and the solution was treated with a solution of hydrogen chloride in ethyl acetate to obtain 0.94 g of a crystal of a hydrochloride showing optical rotation of $+19.1°$ (20° C., sodium D-line, c=1.06 g/dl, methanol).

Physicochemical Properties:

Melting Point: 241°–244° C. (dec.)

Elemental Analysis for $C_{16}H_{17}N_3O.HCl$: Calcd. (%): C 63.26; H 5.97; N 13.83; Cl 11.67 Found (%): C 63.18; H 6.04; N 13.78; Cl 11.45

Mass Spectrum (EI): m/z; 267 (M+, as a free compound)

EXAMPLE 49

Optical Resolution (2) of 5-[(2,3-Dihydroindol-1-yl)carbonyl]-4,5,6,7-tetrahydrobenzimidazole (a) In the same manner as in Example 48(a), except for using (+)-dibenzoyltartaric acid, a crystal of a (+)-dibenzoyltartarate showing optical rotation of $+33.4°$ (20° C. sodium D-line, c=0.60, dimethylformamide) was obtained.

Physicochemical Properties:

Melting Point: 165.0°–166.5° C.

Elemental Analysis for $C_{16}H_{17}N_3O.C_{18}H_{14}O_8.0.7DMF.1.85H_2O$: Calcd. (%): C 61.13; H 5.61; N 7.28 Found (%): C 61.12; H 5.28; N 7.28

Mass Spectrum (EI): m/z; 267 (M+, as a free compound)

(b) In the same manner as in Example 48(b), except for using the salt as obtained in (a) above, a base showing optical rotation of $+7.9°$ (20° C., sodium D-line; c=1.06, methanol) was obtained as a foam-like substance.

Physicochemical Properties:

Melting Point: 98°–103° C.

Elemental Analysis for $C_{16}H_{17}N_3O.0.15AcOEt.0.5-H_2O$: Calcd. (%): C 68.86; H 6.68; N 14.51 Found (%): C 68.65; H 6.66; N 14.45

Mass Spectrum (EI): m/z; 267 (M+)

(c) In the same manner as in Example 48(c), except for using the foam-like base as obtained in (b) above, a crystal of a hydrochloride having optical rotation of $-19.2°$ (20° C. sodium D-line, c=1.07; methanol) was obtained.

Physicochemical Properties:

Melting Point: 239°–242° C. (dec.)

Elemental Analysis for $C_{16}H_{17}N_3O.HCl$: Calcd. (%): C 63.26; H 5.97; N 13.83; Cl 11.67 Found (%): C 63.07; H 5.99; N 13.76; Cl 11.58

Mass Spectrum (EI): m/z; 267 (M+, as a free compound)

EXAMPLE 50

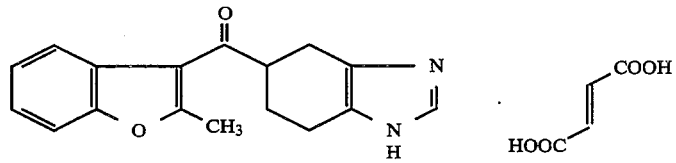

In 40 ml of acetonitrile was suspended 5.00 g of 4,5,6,7-tetrahydrobenzimidazole-5-carboxylic acid sulfate, and 2.75 ml of thionyl chloride was added to the suspension. The suspension was stirred at 55° C. for 1 hour, and the solvent was distilled off under reduced pressure. To the residue was added 20 ml of nitrobenzene and 1.80 ml of 2-methylbenzofurane, and 2.20 ml of tin tetrachloride was then added thereto. After stirring at 85° C. for one night, 40 ml of 1M aqueous hydrochloric acid solution and 40 ml of ethyl ether were added thereto. The organic layer was removed, 40 ml of chloroform was added and then the solution was adjusted to a pH of 9 with 10% aqueous solution of sodium hydroxide. The reaction solution was filtered through celite and then extracted with chloroform containing 10% methanol. The organic layer was collected and the solvent was distilled off. To the free base of objective product obtained by treating the residue with silica gel column chromatography using chloroform/methanol was added calculated amount of fumaric acid to convert it to a fumarate and recrystallized from ethanol to obtain 0.14 g of 5-[(2-methylbenzofuran-3-yl)carbonyl]-4,5,6,7-tetrahydrobenzimidazole fumarate.

Physicochemical Properties:

Melting Point: 188°–189° C.

Elemental Analysis for $C_{17}H_{16}N_2O_2\cdot C_4H_4O_4$: Calcd. (%): C 63.63; H 5.09; N 7.07 Found (%): C 63.47; H 5.06; N 7.01

Mass Spectrum (EI): m/z; 280 (M+, as a free compound)

EXAMPLE 51

5-[(indolizin-3-yl)carbonyl]-4,5,6,7-tetrahydrobenzimidazole

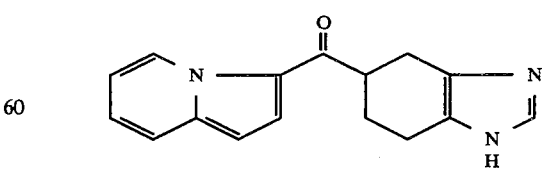

In the same manner as in Example 39, except for replacing 2-methylindolizine with indolizine, above-mentioned compound was obtained.

Physicochemical Properties:

Melting Point: 210°–212° C.

Elemental Analysis for $C_{16}H_{15}N_3O.0.1\ H_2O$ Calcd. (%): C 71.94; H 5.74; N 15.73 Found (%): C 72.08; H 5.79; N 15.67

Mass Spectrum (EI): m/z; 265 (M+)

EXAMPLE 52

5-[(1-methylindolizin-3-yl)carbonyl]-4,5,6,7-tetrahydrobenzimidazole

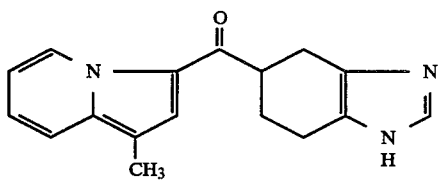

In the same manner as in Example 39, except for replacing 2-methylindolizine with 1-methylindolizine, above-mentioned compound was obtained.

Physicochemical Properties:

Melting Point: 122°–123° C.

Elemental Analysis for $C_{17}H_{17}N_3O.0.25\ C_4H_{10}O.0.4\ H_2O$ Calcd. (%): C 70.87; H 6.71; N 13.77 Found (%): C 70.88; H 6.68; N 13.66

Mass Spectrum (EI): m/z; 279 (M+)

FORMULATION EXAMPLE 1 (Tablets)

| | |
|---|---|
| Compound of Example 44 (hereinafter referred to Compound A) | 0.2 mg |
| Lactose | 106.4 mg |
| Corn starch | 48.0 mg |
| Hydroxypropyl cellulose | 4.8 mg |
| Magnesium stearate | 0.6 mg |
| Total: | 160.0 mg/tablet |

Compound A (200 mg), lactose (106.4 mg), and corn starch (48 g) were uniformly mixed, and 48 ml of a 10% aqueous solution of hydroxypropyl cellulose was added thereto. The mixture was granulated by means of a granulator. To the granules was added 0.6 g of magnesium stearate, and the mixture was punched to obtain 1,000 tablets each weighing 160 mg.

FORMULATION EXAMPLE 2 (Powders)

| | |
|---|---|
| Compound A | 0.4 mg |
| Mannitol | 770.0 mg |
| Corn starch | 199.6 mg |
| Polyvinylpyrrolidone | 30.0 mg |
| Total: | 1,000.0 mg |

Compound A (0.4 g), mannitol (770 g), and corn starch (199.6 g) were uniformly mixed, and 300 ml of a 10% aqueous solution of polyvinylpyrrolidone was added thereto, followed by granulation by means of a granulator to prepare 1 kg of powders.

FORMULATION EXAMPLE 3 (Capsules)

| | |
|---|---|
| Compound A | 0.2 mg |
| Corn Starch | 198.8 mg |
| Calcium stearate | 1.0 mg |
| Total: | 200 mg |

Compound A (0.2 g), corn starch (198.8 g), and calcium stearate (1 g) were uniformly mixed, and the mixture was charged in No. 3 capsules by 200 mg to prepare 1,000 capsules.

FORMULATION EXAMPLE 4 (Syrups)

| | |
|---|---|
| Compound A | 0.2 mg |
| Sucrose | 8.0 mg |
| Pure water to make | 5 ml |

Compound A (0.2 g) and sucrose (8 g) were dissolved in distilled water to prepare 5 l of a syrup.

FORMULATION EXAMPLE 5 (Injections)

| | |
|---|---|
| Compound A | 0.3 mg |
| Sodium chloride | 9 mg |
| Injectable distilled water to make | 1.0 ml |

Compound A (300 mg) and sodium chloride (9 g) were dissolved in injectable distilled water to prepare 1000 ml of a solution. The solution was filtered and charged in 1000 ampules of 1 ml while displacing the atmosphere of the ampule with nitrogen gas. The ampules were sterilized by autoclaving.

EXAMPLE 53

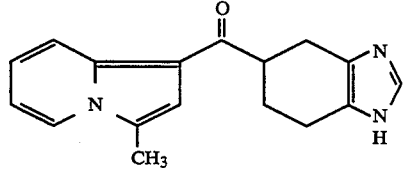

(1) To 10 ml of dichloroethane were added 1.08 g of 5-pyrrolidinocarbonyl-4,5,6,7-tetrahydrobenzimidazole hydrochloride and 1.18 ml of phosphorus oxychloride, and the mixture was stirred at 80° C. for 1 hour. At the same temperature 0.69 g of 3-methylindolizine in 2 ml of dichloroethane was added dropwise thereto during 15 minutes. The mixture was refluxed while stirring for 3 hours after that the mixture was poured into 20 ml of ice-water, and then the mixture was stirred at room temperature for 30 minutes. After liquid-liquid separation, the aqueous layer was washed with 10 ml of dichloromethane. Further, the aqueous layer was adjusted to a pH of about 9 with an aqueous 20% sodium hydroxide solution and then extracted with 20 ml of chloroform-methanol (4:1) twice. The organic layer was dried over anhydrous magnesium sulfate, and the solvent was removed off under reduced pressure. The residue was washed with 20 ml of dichloromethane-ethylacetate (3:1) to obtain 1.00 g of 5-[(3-methylindolizin-1-yl)carbonyl]-4,5,6,7-tetrahydrobenzimidazole.

Physicochemical Properties:

Melting Point: 219°–221° C.

Elemental Analysis for $C_{17}H_{17}N_3O.0.05AcOEt.0.1\ H_2O$ Cacld. (%): C 72.35; H 6.21; N 14.72 Found (%): C 72.42; H 6.18; N 14.84

Mass Spectrum (EI): m/z 279 (M+)

(2) 0.56 g of compound as obtained in (1) was dissolved in 10 ml of ethanol-ethylacetate (4:6), and 0.5 ml of 4N hydrogenchloride-ethylacetate solution was added thereto. The thus formed crystals were collected and the crystals were recrystallized from ethanol to obtain 0.33 g of 5-[(3-methylindolizin-1-yl)carbonyl]-4,5,6,7-tetrahydrobenzimidazole hydrochloride.

Physicochemical Properties
Melting Point: 250°–255 °C. (decomposition)
Elemental Analysis for $C_{17}H_{17}N_3O \cdot HCl$ Cacld. (%): C 64.66; H 5.75; N 13.31; Cl 11.23 Found (%): C 64.43; H 5.85; N 13.21; Cl 11.14

Mass Spectrum (EI): m/z 279 ($M^+$, as a free compound)

While the invention has been described in detail and with reference to specific embodiments thereof, it will be apparent to one skilled in the art that various changes and modifications can be made therein without departing from the spirit and scope thereof.

What is claimed is:

1. A tetrahydrobenzimidazole derivative represented by formula (I):

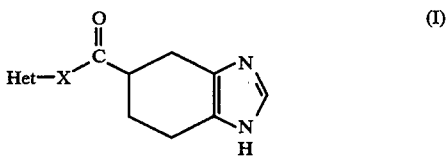

wherein Het represents a member selected from the group consisting of pyrollidine, piperidine, piperazine, morpholine, pyrrole, furan, thiophene, imidazole, oxazole, thiazole, pyrazole, isoxazole, isothiazole, triazole, thiadiazole, oxadiazole, pyridine, pyridazine, pyrimidine, pyrazine, 4H-cyclopentathiazole, indole, isoindole, 2,3-dihydroindole (indoline), isoindoline, hydroxyindole, indazole, indolizine, benzothiophene, benzofuran, benzothiazole, benzimidazole, benzoxazole, 4,5,6,7-tetrahydrobenzothiophene, 2,3-dihydrobenzimidazol-2-one, quinoline, isoquinoline, 1,2,3,4-tetrahydroquinoline, 1,2,3,4-tetrahydroisoquinoline, 1,4-benzoxazine, phenothiazine, carbazole and β-carboline, and wherein Het may be substituted with 1 to 3 substituents selected from the group consisting of lower alkyl, lower alkenyl, lower alkynyl, cycloalkyl-lower alkyl, aralkyl, lower alkoxy, nitro, hydroxyl, lower alkoxycarbonyl, and halo; and X represents a single bond or —NH— which is bonded to the carbon atom or nitrogen atom of the heterocyclic ring of said Het, or a pharmaceutically acceptable salt thereof.

2. The derivative as claimed in claim 1 wherein X represents a single bond.

3. The derivative as claimed in claim 1 wherein X represents a single bond connected to a nitrogen atom of the Het group.

4. The derivative as claimed in claim 1 wherein X represents —NH—.

5. The derivative as claimed in claim 1 wherein Het is pyrrolidinyl.

6. The derivative as claimed in claim 1 wherein Het is 1,2,3,4-tetrahydroisoquinolinyl.

7. The derivative as claimed in claim 1 wherein Het is 2,3-dihydrobenzimidazol-2-one-yl.

8. The derivative as claimed in claim 1 wherein Het is N-(2-benzothiazolyl).

9. The derivative as claimed in claim 1 wherein Het represents a member selected from the group consisting of pyrrolidine, pyrrole, furan, thiophene, imidazole, pyrazole, isoindole, 2,3-dihydrobenzimidazole-2-one, isoindoline, hydroxyindole, indazole, benzothiophene, benzofuran, benzimidazole, 4,5,6,7-tetrahydrobenzothiophene, carbazole and beta-carboline.

10. The derivative as claimed in claim 1 wherein Het is indole.

11. The derivative as claimed in claim 1 wherein Het is 2,3-dihydroindol.

12. A compound as claimed in claim 1, wherein Het is represented by the formula:

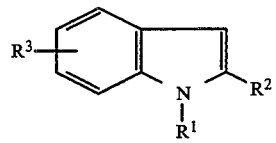

wherein $R^1$ represents hydrogen, lower alkyl, lower alkenyl, lower alkynyl, cycloalkyl-lower alkyl, or an aralkyl; $R^2$ represents hydrogen, lower alkyl, or aralkyl; and $R^3$ represents hydrogen, lower alkoxy, nitro, hydroxyl, lower alkoxycarbonyl, or halo; and X represents a single bond.

13. A compound as claimed in claim 1, wherein Het represents a nitrogen-containing heterocyclic group; and X is a single bond connected to the nitrogen atom of the nitrogen-containing heterocyclic ring.

14. A compound as claimed in claim 12, wherein said compound is 5-[(1-methylindol-3-yl)carbonyl]-4,5,6,7-tetrahydrobenzimidazole.

15. A compound as claimed in claim 1, wherein said compound is an (R)-compound.

16. A compound as claimed in claim 1, wherein said compound is an (S)-compound.

17. A compound as claimed in claim 1, wherein said compound is 5-[[1-(2-propynyl)indol-3-yl]carbonyl]-4,5,6,7-tetrahydrobenzimidazole.

18. A compound as claimed in claim 1, wherein said compound is 5-[(2,3-dihydroindol-1-yl)carbonyl]-4,5,6,7-tetrahydrobenzimidazole.

19. A compound as claimed in claim 1, wherein said compound is 1-[(4,5,6,7-tetrahydrobenzimidazole-5-Yl)carbonyl]-2,3-dihydrobenzimidazol-2-one.

20. A compound as claimed in claim 1, wherein said compound is 5-[(2-benzylindol-3-yl)-carbonyl]-4,5,6,7-tetrahydrobenzimidazole.

21. A compound as claimed in claim 1, wherein said compound is 5-[(1-n-butylindol-3-yl)carbonyl]-4,5,6,7-tetrahydrobenzimidazole.

22. A compound as claimed in claim 1, wherein said compound is 5-[(1-cyclohexylmethylindol-3-yl)carbonyl]-4,5,6,7-tetrahydrobenzimidazole.

23. A compound as claimed in claim 1, wherein said compound is 5-[1-benzylindol-3-yl)carbonyl]-4,5,6,7-tetrahydrobenzimidazole.

24. A compound as claimed in claim 1, wherein said compound is N-(pyridin-3-yl)-4,5,6,7-tetrahydrobenzimidazole-5-carboxamide.

25. A compound as claimed in claim 1, wherein said compound is N-(5,6-dihydro-4H-cyclopentathiazol-2-yl)-4,5,6,7-tetrahydrobenzimidazole-5-carboxamide.

26. A pharmaceutical composition containing a tetrahydrobenzimidazole derivative represented by the following formula (I) or a pharmaceutically acceptable salt thereof:

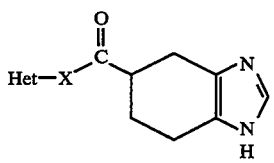 (I)

wherein Het represents a member selected from the group consisting of pyrrolidine, piperidine, piperazine, morpholine, pyrrole, furan thiophene, imidazole, oxazole, thiazole, pyrazole, isoxazole, isothiazole, triazole, thiadiazole, oxadiazole, pyridine, pyridazine, pyrimidine, pyrazine, 4H-cyclopentathiazole, indole, isoindole, 2,3-dihydroindole (indoline), isoindoline, hydroxyindole, indazole, indolizine, benzothiophene, benzofuran, benzothiazole, benzimidazole, benzoxazole, 4,5,6,7-tetrahydrobenzothiophene, 2,3,-dihydrobenzimidazol-2-one, quinoline, isoquinoline, 1,2,3,4-tetrahydroquinoline, 1,2,3,4-tetrahydroisoquinoline, 1,4-benzoxazine, phenothiazine, carbazole and β-carboline, and wherein Het may be substituted with 1 to 3 substituents selected from the group consisting of lower alkyl, lower alkenyl, lower alkynyl, cycloalkyl lower alkyl aralkyl, lower alkoxy, nitro, hydroxyl, lower alkoxycarbonyl, and halo; and X represents a single bond or —NH— which is bonded to the carbon atom or nitrogen atom of the heterocyclic ring, and a pharmaceutically acceptable carrier.

27. A pharmaceutical composition as claimed in claim 26, wherein said composition is a 5HT$_3$-antagonist.

28. A pharmaceutical composition as claimed in claim 26, wherein said composition is a treating agent for gastrointestinal disorders.

29. A pharmaceutical composition as claimed in claim 26, wherein said gastrointestinal disorders are anaphylactic intestinal syndrome.

30. A pharmaceutical composition as claimed in claim 26, wherein said composition is a treating agent for nausea and/or vomiting induced by chemotherapy or radiation.

31. A pharmaceutical composition as claimed in claim 26, wherein said composition is a treating agent for migraine, cluster headache and trigeminal neuralgia.

32. A pharmaceutical composition as claimed in claim 26, wherein said composition is a treating agent for anxiety and psychotic disorders.

* * * * *